US005731112A

United States Patent [19]

Lewis et al.

[11] Patent Number: 5,731,112
[45] Date of Patent: Mar. 24, 1998

[54] PROCESSLESS DIACETYLENIC SALT FILMS CAPABLE OF DEVELOPING A BLACK IMAGE

[75] Inventors: David F. Lewis, Monroe, Conn.; Sangya S. Varma, Bedminster, N.J.

[73] Assignee: ISP Investments Inc., Wilmington, Del.

[21] Appl. No.: 652,144

[22] Filed: May 23, 1996

[51] Int. Cl.⁶ ................................................. G03C 1/735
[52] U.S. Cl. ............................. 430/15; 430/17; 430/333; 430/336; 430/338
[58] Field of Search ........................ 430/15, 17, 292, 430/293, 296, 333, 336, 338, 349, 351; 562/595, 598

[56] References Cited

U.S. PATENT DOCUMENTS

| | | |
|---|---|---|
| 3,501,297 | 3/1970 | Cremeans et al. |
| 3,501,302 | 3/1970 | Foltz et al. |
| 3,501,303 | 3/1970 | Foltz et al. |
| 3,501,308 | 3/1970 | Adelman et al. |
| 3,679,738 | 7/1972 | Cremeans. |
| 3,723,121 | 3/1973 | Hauser et al. |
| 3,743,505 | 7/1973 | Bloom et al. |
| 3,772,011 | 11/1973 | Guevara et al. |
| 3,772,027 | 11/1973 | Luckey et al. |
| 3,772,028 | 11/1973 | Fico et al. |
| 3,794,491 | 2/1974 | Borsenberger et al. |
| 3,810,778 | 5/1974 | Wang. |
| 3,811,895 | 5/1974 | Ehrlich. |
| 3,822,134 | 7/1974 | Rasch et al. |
| 3,836,368 | 9/1974 | Jun et al. |
| 3,844,791 | 10/1974 | Bloom et al. |
| 3,954,816 | 5/1976 | Bloom et al. |
| 3,999,946 | 12/1976 | Patel et al. |
| 4,066,676 | 1/1978 | Bloom et al. |
| 4,125,534 | 11/1978 | Yee. |
| 4,189,399 | 2/1980 | Patel. |
| 4,208,501 | 6/1980 | Yee et al. |
| 4,215,208 | 7/1980 | Yee et al. |
| 4,235,108 | 11/1980 | Patel. |
| 4,238,352 | 12/1980 | Patel. |
| 4,242,440 | 12/1980 | Yee et al. |
| 4,247,613 | 1/1981 | Ott. |
| 4,339,951 | 7/1982 | Yee et al. |
| 4,439,514 | 3/1984 | Garito. |
| 4,452,959 | 6/1984 | Kobayashi et al. |
| 4,452,995 | 6/1984 | Patel. |
| 4,536,450 | 8/1985 | Garito. |
| 4,562,141 | 12/1985 | Tieke. |
| 4,581,315 | 4/1986 | Garito. |
| 4,698,296 | 10/1987 | Lewis. |
| 4,705,741 | 11/1987 | Lewis et al. |
| 4,705,742 | 11/1987 | Lewis. |
| 4,784,934 | 11/1988 | Lewis et al. |
| 4,789,622 | 12/1988 | Leyrer et al. |
| 4,863,832 | 9/1989 | Saitoh et al. |
| 5,049,428 | 9/1991 | Kanno et al. |
| 5,095,134 | 3/1992 | Liu. |
| 5,137,964 | 8/1992 | Lewis et al. |
| 5,139,927 | 8/1992 | Liu. |
| 5,139,928 | 8/1992 | Lewis. |
| 5,149,616 | 9/1992 | Liu. |
| 5,149,617 | 9/1992 | Liu. |
| 5,153,106 | 10/1992 | Liu. |
| 5,158,862 | 10/1992 | Liu. |
| 5,215,869 | 6/1993 | Liu. |
| 5,215,870 | 6/1993 | Liu. |
| 5,232,820 | 8/1993 | Lewis et al. |
| 5,481,002 | 1/1996 | Fischer et al. |

FOREIGN PATENT DOCUMENTS 2-091106  3/1990  Japan.

OTHER PUBLICATIONS

*Die Makromoleculare Chemie*, 154, 35–48 (1972).

*Primary Examiner*—John A. McPherson
*Attorney, Agent, or Firm*—Jules E. Goldberg; Marilyn J. Maue; Joshua J. Ward

[57] ABSTRACT

This invention relates to a mixture of imageable polyacetylenic compounds which have similar photosensitivities and which are visually imageable in complementary colors combinable to provide a black image, which mixture contains at least one polyacetylenic metal salt which produces a color, preferably a metal salt of a diacetylene $C_6$ to $C_{48}$ mono- or dicarboxylic acid, which is complementary to a color produced by another polyacetylenic metal salt or non-metallic polyacetylenic compound contained in the mixture or in an another integral color forming layer. The invention also pertains to the use of said mixture and the manner of its preparation.

92 Claims, No Drawings

PROCESSLESS DIACETYLENIC SALT FILMS CAPABLE OF DEVELOPING A BLACK IMAGE

BACKGROUND OF THE INVENTION

Much of the black on white photographic industry depends on the use of silver salts, e.g. mixed halides, as the active agent. One characteristic of the silver process is its high photosensitivity achieved through amplification; however, this benefit is realized at some sacrifice to resolution. Further, images of high acuity and density require liquid chemical processing with inherent process limitations and environmental drawbacks. In contrast, polyacetylene-based, "processless" films are imaged solely by the application of one or more simple physical means, such as by exposure to ionizing radiation which provides instantaneous imprinting at 1000 lines/mm, or higher resolution, at a high density. Alternatively, a first simple physical means of exposure to thermal radiation can cause latent-image formation by the deactivation of the polyacetylene imaging component. The final image can then be developed by a second simple physical means of exposure to ionizing radiation. In both cases, not only does this mode of imaging reduce the time for obtaining an imaged product, but also it avoids safety and environmental problems associated with chemical development, eliminates the cost of such processing and increases the quality and efficiency of imaging.

Notwithstanding the benefits of polyacetylenic films, the majority of diacetylenic compounds which are capable of color development produce blue, purple, magenta, and red coloration; yellow being less common and pure permanent black being virtually unknown. Further complicating the issue of a chosen color development is the widely varying photosensitivity of the individual color producing diacetylenes.

OBJECTS OF THE INVENTION

It is an object of the present invention to provide a polyacetylenic-based film which is imageable to a black or neutral near black color in high density.

Another object of the invention is to provide a photosensitive, thermochromic polyacetylenic film which is imageable to a black or near black color by exposure to ionizing radiation and heat.

Still another object is to provide economic and commercially feasible processes for the production of such black or neutral near black imageable films suitable for use in recording media.

These and/or other objects may be readily gleaned from a review of the following description and disclosure of the present invention.

BRIEF DESCRIPTION OF THE INVENTION

The polyacetylene compounds of the present invention contain the conjugated chemical group $(-C{\equiv}C-)_n$ (generally, where n=2 to 6, preferably 2 to 4 and more preferably 2) and generally exist in an ordered state as in crystals or in an oriented monolayer. These crystalline or oriented polyacetylenes are capable of intermolecular alignment which is provided through specific chemical ions, atoms or groups attached to the polyacetylene moiety and are capable of undergoing solid state polymerization to polyacetylene polymers (generally, by way of 1,4 addition-type reactions) by exposure of the monomeric polyacetylene compounds to ionizing radiation. These chemical ions, atoms or groups provide molecular alignment in the crystal structure so that only a small atomic motion within the polyacetylene unit is required to effect polymerization.

It is now discovered that intermixtures or discrete integral layers of certain imageable polyacetylene metal salts or mixtures of a metal salt and a non-metal salt polyacetylenic compound which form images in complementary colors after polymerization (e.g. blue-yellow, magenta-green, cyan-red, etc.), are capable of producing a permanent black or neutral near black image color upon exposure of mixtures containing these polyacetylenic components to ionizing radiation followed by heat. In preferred embodiments, the black image color is produced by first exposing the intermixture or discrete layers to ionizing radiation followed by a second step which exposes the intermixture or layers to thermal radiation. In a more preferred embodiment, a single metal salt of a polyacetylene carboxylic acid may be used to generate the permanent black or near black image color.

In other preferred embodiments, the black image color may be produced after a first thermal radiation step is used to inactivate certain portions of polyacetylenic compounds in a mixture, a second step of exposure to ionizing radiation, followed by a third step of exposure to heat or thermal radiation. Using this method, the black image color which is formed after the second thermal radiation step will appear in combination with a colorless or white area which is formed by inactivating a portion of the mixture with a first thermal radiation step, thus highlighting the black image color produced.

In other preferred embodiments according to the present invention the permanent black or near black image color is produced by the complementary colors blue and yellow.

Compositions according to the present invention may be used to produce high resolution laser scanning film, to produce high resolution images in laser printing applications and to produce continuous tone photographic images, among numerous other uses.

DETAILED DESCRIPTION OF THE INVENTION

The following definitions will be used throughout the specification in order to describe the present invention.

The term "permanent black or near black image color" as employed herein refers to an image which appears black or near black and which is non-reversible, i.e., it is not further imageable to another color. The desired result which is obtained by the implementation of the present invention is the production of a permanant black or near black image color, preferably in the shape or form of a design. It is also contemplated, however, that the black image color may appear as a background surrounding a light colored, colorless or even white image in the form of a design.

The term "imageable" is used throughout the description of the present invention to describe a composition, film, mixture, laminate, etc. which contains polyacetylene compounds which, upon exposure to ionizing radiation, will produce a color image. The terms "photochromic", "photosensitive thermochromic" and "thermochromic" are subsets of the term imageable and relate generally to the type of energy or radiation which may be used to produce a color or image from the polyacetylene compounds according to the present invention. For example, a photochromic compound is a compound which produces an image color using an effective amount of ionizing radiation and/or visible light (i.e., in a concentration and for a duration of time) to produce the image color. A photosensitive thermochromic compound is a compound which may produce such an image color using effective amounts of ionizing radiation and/or visible light and heat. A thermochromic compound is a compound which produces a color image by exposing the compound to effective amounts of heat, i.e., an amount of heat which is effective to produce an image color. Polyacetylene compounds according to the present invention preferably are thermochromic, i.e., they produce the black or near black image after exposing the compound to heat. In many instances, according to the present invention, the black or near-black image is produced by first exposing the polyacetylenic compound(s) to effective amounts of ionizing radiation (which term includes visible light) followed by a second heat step.

The term "ionizing radiation" is used throughout the specification to describe energy in any form (other than thermal or heat energy) to which polyacetylenic compounds according to the present invention are exposed in a first step (the second step being a heat step) in order to generate the permanent black or near black image colors of the present invention. In general, the term ionizing radiation embraces all forms of radiation other than thermal radiation which may be used in a first step in producing the final black or near black image. Ionizing radiation generally is energy in the form of radiation having an effective wavelength below about 400 nm. Sources of ionizing radiation include, for example, radiation generated from an electron beam, a mercury xenon arc lamp, a mercury arc lamp, a xenon flash lamp, actinic light, neutrons, X-rays, gamma rays, beta rays, alpha particles, electron corona discharge, or a UV laser or other UV light source capable of polymerizing the crystalline photosensitive acetylenic component(s) to the corresponding imageable homopolymer(s); thus creating a positive, visible colored reproduction of the image being transmitted. The term ionizing radiation also includes energy in the form of visible light or obtained from visible light sources, which may also be used in a first step to generate the black or near black image colors according to the present invention.

The term "complementary colors" as employed herein refers to a combination of colors overlaid or intermixed which, produce a permanent black or neutral near black image color according to the present invention. The color which a compound produces relates to that portion of the visible light spectrum which is transmitted by the compound, the remaining portion of the visible spectrum being absorbed by the compound. The term complementary colors is derived from the use of two or more compounds or isomers which, between them, will essentially absorb the entire visible spectrum, thus producing a permanent black or near-black image color. "Complementary dyes" are two or more dyes according to the present invention which produce complementary colors and consequently, a permanent black or neutral near black image color when combined. Complementary colors which are used in the present invention include, for example, blue and yellow; magenta and green; cyan and red; etc.

The term "polyacetylene compound, component or monomer" is used to describe polyacetylenic precursors which are used in the present invention to ultimately produce polymeric compounds ("polyacetylene polymers" as described in greater detail hereinbelow) which produce the desired black or near-black image. These polyacetylene compounds contain the conjugated chemical group $-(C\equiv C)_n-$ (generally, where n=2 to 6, preferably 2 to 4 and more preferably 2). In the present invention, the diacetylenes (n=2) are preferred. The term includes conjugated metal salt polyacetylenes of the present invention.

The term "diacetylene compound, component or monomer" is used throughout the specification to describe the metal and non-metal diacetylenic compounds which are used in the present invention to produce a permanent black or near black image color from complementary colors. Most of these diacetylenic components used in the present invention are prepared and used in crystalline form. The term diacetylene component or diacetylenic compound is a subset of the term "polyacetylene" or "polyacetylenic compound component or monomer".

The term "complementary polyacetylene component" or "complementary polyacetylenic component" is used throughout the specification to describe various metal salts and/or combinations of metal salt and non-metal polyacetylenic compounds, components or monomers which are used together to produce a permanent black or neutral near black color. These polyacetylene components generally (but not exclusively) produce polyacetylene polymers which individually provide a complementary color and a resultant black image color to the film(s) containing these polyacetylene polymers.

The term "polyacetylene metal salt" or "metal salt of a polyacetylene" is used throughout the specification to refer to metal salts of polyacetylene (preferably including di-, tri- and tetra-acetylene) compounds which produce a color after being exposed to ionizing radiation and/or thermal radiation (generally, but not exclusively following formation of polyacetylene polymers). The term polyacetylene metal salt includes diacetylene metal salt, which are preferred for use in the present invention. Preferred polyacetylene metal salts for use in the present invention include mono- and polyvalent metal salts of polyacetylene monocarboxylic or dicarboxylic acids, preferably $C_6$ to $C_{48}$ mono- or dicarboxylic acids (preferably diacetylenic carboxylic acids of the aforementioned carbon chain lengths), more preferably $C_{14}$ to $C_{48}$ mono- or dicarboxylic acids and even more preferably metal salts of polyacetylene $C_{15}$ to $C_{35}$ mono- or dicarboxylic acids. Particularly preferred monocarboxylic or dicarboxylic acids for use in the present invention are diacetylenic mono- or di-carboxylic acids of carbon chain length $C_{20}$ to $C_{29}$ with monocarboxylic acids being preferred.

The term "polyacetylene carboxylic acid" is used throughout the specification to describe polyacetylenic mono- or di-carboxylic acid compounds. Preferred polyacetylenic carboxylic acids according to the present invention have the chemical formula which corresponds to a carbon chain length ranging from $C_6$ to $C_{48}$:

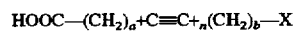

where

X=H, an aryl group (especially phenyl) or COOH;

n is 2 to 6, more preferably 2 to 4, most preferably 2;

a is an integer from 0 to 24; and b is an integer from 0 to 24, such that $0 \leq a+b \leq 34$ when X is aryl or COOH and $1 \leq a+35$, when X is H.

Monocarboxylic acids having a carbon chain length preferably ranging from $C_{14}$ to $C_{43}$ have the general formula:

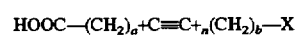

where

X is aryl (especially phenyl) or H;

n is 2 to 6, more preferably 2 to 4, most preferably 2;

a is an integer from 0 to 19; and b is an integer from 0 to 19, such that $9 \leq a+b \leq 29$.

Preferred polyacetylene carboxylic acids for use in the present invention are diacetylene carboxylic acids where a is preferably 2, 3, 6, or 8, corresponding to acetylene groups at 4,6; 5,7; 8,10 and 10,12 of the polyacetylene carboxylic acid. More preferably, a is 3,6 or 8, even more preferably 3 or 8 and most preferably 3.

The polyacetylene carboxylic acids are preferably $C_6$ to $C_{48}$ mono- or dicarboxylic acids (preferably diacetylenic carboxylic acids of the aforementioned carbon chain lengths), more preferably polyacetylene $C_{14}$ to $C_{43}$ mono- or dicarboxylic acids, even more preferably polyacetylene $C_{15}$ to $C_{35}$ mono- or dicarboxylic acids. Particularly preferred monocarboxylic or dicarboxylic acids for use in the present invention are diacetylenic mono- or di-carboxylic acids of carbon chain length $C_{20}$ to $C_{29}$ with monocarboxylic acids being preferred. The polyacetylene monocarboxylic acids are generally preferred over the dicarboxylic acids. It is noted that the polyacetylene carboxylic acids useful in the present invention are not limited to the above-described chemical formulas, which are merely preferred. The polyacetylene carboxylic acids which find use in the present invention may contain very long carbon chains (i.e., greatly in excess of 40 carbon units) with the limitation being determined by the final physical or chemical characteristics of the compounds (such as solubility) and the amount of compound which would be required to be added in order to generate a color of sufficient intensity (which may, in certain instances, be related to the molecular weight of the polyacetylenic component used). Metal salts of the polyacetylene carboxylic acids, and in particular, zinc salts of these monocarboxylic acids are more preferred for use in the present invention. The zinc salt of eicosa-5,7-diynoic acid is most preferred for use in the present invention.

The term "unbranched" or "linear" is used to describe preferred polyacetylene compounds, in particular, polyacetylenic carboxylic acids, used in the present invention. Unbranched or linear refers to the fact that the polyacetylene compounds (including the polyacetylene carboxylic acids) are found in straight carbon chains and do not contain pendant alkyl groups as branches from the main chain.

The term "metal cation" of the diacetylenic metal salt refers to a mono- or poly-valent metal ion having atomic weights ranging from about 7 to about 180 and include, for example, ions of lithium (Li), magnesium (Mg), calcium (Ca), zinc (Zn), rubidium (Rb), barium (Ba), manganese (Mn), zirconium (Zr), technitium (Te), thalium (Tl) and thulium (Tm) which are used as the counterion to the diacetylene carboxylic acids. Of these, zinc ion, manganese ion, rubidium ion and lithium ion are preferred.

The term "non-metallic polyacetylenic compound" is used throughout the specification to describe an imageable polyacetylene component which does not contain a metal salt. When employed, the non-metallic polyacetylenic compound may be a mono- or di-substituted acid or amine salt thereof, an amide, ester, carbonate, carbamate or cinnamate derivative (each being a mono- or disubstituted derivative) or any other derivative which is imageable by ionizing radiation to a color complementary to the polyacetylene metal salt component such that the resulting image will be a permanent black or near black image color.

The term "metal salt by-product" or "by-product metal salt" is used to describe a salt compound which is a by-product of the ion exchange reaction used to generate or prepare the polyacetylene metal salt.

The term "linear alkyl carboxylate anion" is used to describe an anion which is useful as a component of the image forming layer of this invention, in imparting a neutral, black color to the image. Linear alkyl carboxylates are those having the general formula $X(CH_2)_m—Y—(CH_2)_n—CO_2^-$ where X=H or aryl, Y=—$CH_2$—, —NH— or —O—, m=0 to 13, n=0 to 13 and n+m≦13, most preferably where X=H and m+n=0 to 7.

Non-metallic polyacetylenic compounds which are preferred in the present invention are those which produce a yellow color or image. Inasmuch as many metallic polyacetylenic compounds produce a blue color or image, a non-metallic polyacetylenic compound which produces a complementary yellow image is preferred for use in the present invention. Non-metallic polyacetylenic compounds which are used in the present invention for their ability to produce a yellow or golden-yellow color include those which are reported in U.S. Pat. Nos. 3,723,121; 4,705,742; 5,095,134; 5,139,927; 5,149,616; 6,149,617; 5,158,862; 5,215,869 and 5,215,870. These patents disclose a number of polyacetylene compounds which produce a yellow or golden-yellow color, including, for example, 10,12-docosadiyndioic acid monomer, 5,7-dodecadiyn-1,12-bis (isopropyl carbamate), 1,12-(3,10-dioxa-5,7-dodecadiyne) diyl dicinnamates, such as $(C_6H_5—CH=CHCOOC_2H_4OCH_2—C≡C)_2$, pentacosa-10,12-diynoic acid, the monomethylester of docosadiyne-10,12-dioic acid, and 3,10-dioxa-5,7-dodecadiyn-1,12-bis (isopropyl carbamate), among others.

Urethanyl diacetylenic compounds such as those described in U.S. Pat. No. 4,215,208, which provide golden and green-golden images, including various urethanyl derivatives (including isopropyl, n-butyl, n-hexyl, n-octyl, ethylisocyanatoacetate, n-butylisocyanatoacetate, m-tolyl, p-tolyl, o-chlorophenyl, m-chlorophenyl, p-chlorophenyl and 2-chlorophenyl) of 5,7-dodecadiyn-1,12-diol and 4,6-decadiyn-1,10-diol, among others, are also useful herein as a non-metallic diacetylenic component of the present mixture. The disclosure of these patents are incorporated by reference herein. Numerous other non-metallic polyacetylenic compounds for use in the present invention, which provide non-yellow images, are also incorporated herein as suitable non-metal polyacetylenic components for producing complementary color combinations with a metal salt component of this invention.

The term "polyacetylene polymer" or "polydiacetylene" is used throughout the specification to describe polymeric compounds which result, at least in part, from the polymerization reaction of the polyacetylenic compounds of the present invention. It is the polyacetylene polymers or polyacetylene polymers which are formed from the polymerization of the polyacetylenic compounds and which generally produce the resultant color which provides the desirable permanent black or neutral near black color of the present invention. These polymers are generally formed from 1,4 addition reactions between monomeric polyacetylene compounds.

The term "photosensitivity" or "photochemical sensitivity" is used throughout the specification to describe the relative sensitivity of a compound to produce a color intensity after exposure to radiant energy, preferably in the form of UV light energy in the short wavelength spectrum (about 220 nm to about 300 nm). Preferably, the complementary polyacetylenic components of the present invention have similar photochemical sensitivities in order to insure the proper balance of complementary colors which produces a black color image.

In general, the photosensitivities of the diacetylenic compounds which produce complementary colors according to the present invention range from about 100 nanojoules per square centimeter (100 nj/cm$^2$) to about 100 joules per square centimeter (100 j/cm$^2$), preferably about 1 microjoule per square centimeter (1 µj/cm$^2$)to about 10 j/cm$^2$. These ranges of photosensitivities should serve as a guide, not a limitation to the photosensitivities of the polyacetylenic components used in the present invention. It should be readily recognized that photosensitivities outside of these ranges may also be used in the present invention.

In preferred embodiments according to the present invention, in order to produce a readily reproducible permanent black or neutral near black image color, the photosensitivity of a first polyacetylenic component should range from about 0.1 to about 10 times the photosensitivity of the complementary polyacetylenic component, more preferably about 0.3 to about 3 times the photosensitivity of the complementary polyacetylenic component. Photosensitivities of the first polyacetylenic component which are approximately the same as, i.e., about 0.67 to about 1.5 times the photosensitivity of the complementary polyacetylenic component are particularly preferred for use in the present invention.

Similar photochemical sensitivities (i.e., photosensitivities which preferably fall approximately within the above-described ranges) between or among the polyacetylenic components in a mixture is needed to efficiently achieve the proper color balance which transmits black or near black image colors. More specifically, where the sensitivities of the polyacetylenic components are substantially different, a greater amount or extended exposure of the lower sensitive component is required to arrive at a balance of color which transmits a black image color. Although a balance between such components can be achieved by employing a greater molecular amount or a thicker layer of the less active polyacetylene component, such measures are difficult to determine and execute.

Preferably, the polyacetylenic components of the mixture have similar photosensitivities as described hereinabove, and a distribution of particle sizes ranging from about submicron size to about 10 µm.

The term "color balance" or "balance of color" is used throughout the specification to refer to the ratio of red, green and blue color absorption resulting from a permanent black or near black image color according to the present invention. In the subtractive color system, a blue dye transmits blue light and absorbs green and red light and a yellow dye will transmit red light and green light, but will absorb blue light. A suitable combination of complementary dyes, for example, blue and yellow dyes, will therefore absorb approximately equal amounts of blue, green and red light. The color tone of the transmitted light (assuming white light illumination), is therefore neutral, because the blue/yellow dye combination of the example has modulated the illumination equally in the three primary areas of the color spectrum. The color balance of the transmitted light is said to be neutral or grey.

Deeper or lighter shades of grey may be obtained by providing either larger or smaller amounts of the blue and yellow dye combination, so long as the relative proportions of the blue and yellow dyes are held constant from sample to sample or from one area of the image to another. In such a case, the color tone or color balance of the transmitted light from sample to sample or area to area will be unaltered, and the effect will be to transmit light in a darker or lighter shade of grey. In cases where the proportions of the dyes change, then the perceived color of the particular combination of the dyes will change, as well as the overall intensity of the transmitted light, i.e., the lightness or darkness of the color.

For example, a mid-tone grey color is transmitted with equal proportions of blue and yellow dyes. If, in transmitting a darker grey color, the ratio of blue:yellow dye is also increased, the darker grey color will take on a blue-grey color balance, i.e., the color is biased towards blue. Conversely, if in forming a dark grey color, the proportion of the yellow dye increases relative to blue, the darker grey will take on a yellow-grey color balance, i.e., the color is biased towards yellow.

Ideally, in reproducing various grey tones between white and black, it is desirable that the color balance of the intermediate grey tones be identical to one another.

The term "binder" is used throughout the specification to describe an additive used in combination with the polyacetylenic components to preferably bind to the surface of the polyacetylenic components (which are generally included in final compositions as crystals or in crystalline form), control the growth of crystals, keep the crystals separated and prevent them from agglomerating, and/or adhere the crystals to a substrate or support. The binder is included in the present compositions in amounts which will substantially reduce or eliminate agglomeration of the polyacetylenic crystals. The binder is advantageously included in the present compositions to provide a certain consistency and stability to color generation and will maintain a consistent concentration of the polyacetylenic components in the final compositions as well as have a secondary effect to enhance resolution of the final image. In general, the weight ratio of binder to polyacetylene component will range from about 1:10 to about 10:1. Thus, binder will be included in formulations in amounts ranging from about 10% to about 1000% or more by weight of the polyacetylenic compound(s). In preferred embodiments, the binder is included in a weight ratio of about 1:10 to about 1:1 by weight of the polyacetylenic component.

Preferred binders for use in the present invention include natural and synthetic plastics, resins, waxes, colloids, latices, gels and the like, including for example, gelatins, polymers and copolymers of vinyl pyrrolidone and acrylic-type resins, especially acrylic polymer resins containing acrylic acid residues, among other polymeric materials such as polyvinylacetate, polyvinyl alcohol, other polyvinyl copolymers and styrenic polymers, among others. In addition, binders may include various polysaccharides such as dextran, dextrin, hydrophilic cellulose ethers and esters, acetylated starches, natural and synthetic waxes among numerous others known in the art for use as photographic binders. In compositions according to the present invention, the binder advantageously should have a melting point higher than the temperature at which the present composition is heated to produce the final permanent black image color. The preferred binder should also have the same or a very similar refractive index as that of the crystals of the polyacetylenic components.

Compositions according to the present invention include binder in an amount effective for maintaining the consistency of color in the present compounds. In compositions according to the present invention, the amount of binder to polyacetylenic component generally ranges from about 10% to about 1000% by weight, more preferably about 10% to about 100% by weight.

In certain aspects, the present invention relates to a mixture of metallic polyacetylenic compounds or a metallic polyacetylenic compound and a non-metallic polyacetylenic compound which, when exposed to radiant energy followed by thermal energy, will produce a permanent black or near black image color.

As explained above, the mixtures which may be used in this invention can comprise the combination of two or more metal salts of polyacetylene mono- or di-carboxylic acids or the mixture can be a combination of one or more of said polyacetylenic metal salts with one or more non-metal salt acetylenic compounds capable of imaging in a complementary color.

In certain preferred aspects, the present invention relates to the use of a single metal salt (preferably, a zinc salt) of a polyacetylene mono- or dicarboxylic acid in combination with effective concentrations of nitrate and/or alkylcarboxylate anions. It has unexpectedly been discovered that the inclusion of this combination of a metal salt of a polyacetylene carboxylic acid and an effective concentration of one or more of the above-described anions results in a permanent black or near black image without including an additional polyacetylene component.

The metal ions of the metallic polyacetylenic compound in the present mixture are mono- or poly-valent metals having atomic weights of about 7 to 180. Representative of this latter group are Li, Mg, Ca, Zn, Rb, Ba, Mn, Zr, Tl, Te and Tm. Of these, zinc, manganese, rubidium and lithium salts are preferred for their high sensitivity and/or color density. Zinc is especially preferred. Preferably, the present metallic polyacetylenic compounds are the zinc, manganese, lithium or rubidium salt derivatives of polyacetylene $C_6$ to $C_{48}$ mono- or dicarboxylic acids; zinc, lithium and rubidium metal salts of the n-alkyl. $C_{14}$ to $C_{43}$ mono- or dicarboxylic acids being more preferred(monocarboxylic acids being even more preferred), with zinc salts of these carboxylic acids (mono- or di-) being most preferred.

When employed, the non-metallic polyacetylene component of the mixture can be selected from a mono- or di-carboxylic acid, an amide, ester, carbonate, carbamate or cinnamate derivative (each of these preferably as a mono- or di-functionalized derivative) or it can be any other derivative which is imageable by exposure to ionizing radiation to a color complementary to the color of the metal salt component culminating in a black image color. $C_{14}$ to $C_{43}$ polyacetylenic monocarboxylic acid non-metal salt derivatives are particularly useful for color balance and activity in mixtures with metal salt components.

In using the non-metallic acetylenic compound, mixed crystals of non-metallic diacetylene carboxylic acids having different hydrocarbon chain lengths are found to exhibit synergistic properties in an unexpectedly high photosensitivity. Mixtures of the zinc bis ($C_{20}$ to $C_{29}$) diynoates and an unbranched diynoic acid of approximately equal chain length or a mixture of such unbranched diynoic acids have been found to provide superior black images.

In particularly preferred embodiments according to the present invention a zinc metal salt of a $C_6$ to $C_{48}$ diacetylenic mono- or dicarboxylic acid, more preferably, a $C_{14}$ to $C_{43}$ diacetylenic mono- or dicarboxylic acid, even more preferably a $C_{14}$ to $C_{43}$ diacetylenic monocarboxylic acid and even more preferably zinc bis(eicosa-5,7-diynoate), is combined with an effective concentration of an additive selected from the group consisting of a nitrate ($NO_3^-$) anion, a linear alkylcarboxylate anion or preferably, mixtures, thereof. In certain embodiments, the inclusion of the sodium salt compounds of the aforementioned anions is particularly advantageous. For purposes of this aspect of the present invention, an effective concentration of the anionic compound is that amount of anion, which, in combination with the zinc metal salt of the diacetylenic carboxylic acid, will produce an irreversible yellow color upon exposing the mixture of salt and anion first to ionizing radiation followed by heat energy at a temperature sufficient to produce a yellow color (preferably, at least about 50° C., more preferably, at least about 100° C. up to a temperature of less than about 500° C., more preferably less than about 200° C.). The resultant yellow color is complementary to the blue colors produced by many metallic and non-metallic polyacetylenic compounds, thus providing a ready means to form the desirable permanent black or near black images of the present invention.

This aspect of the present invention takes advantage of the thermochromic transition properties of the polymerized zinc metal salts of $C_6$ to $C_{48}$ diacetylenic carboxylic acids, preferably, the polymerized zinc salt of pentacosa-10,12-diynoic acid and eicosa-5,7-diynoic acid, each of which produces a blue color upon photoexposure. Specifically, in the presence of an effective concentration of the sodium salt of a linear alkylcarboxylate anion and/or nitrate anion (the concentration of the anion generally ranges from about 4:1 to about 1:20, more preferably about 1:1 to about 1:8 by weight of the zinc metal salt), the zinc polydiacetylene salt exhibits an irreversible blue to yellow color change at about 100° C. or above. In this embodiment, when the zinc polydiacetylene salt is instead combined with zinc ion such that the zinc ion is present at an excess concentration, i.e., in significant excess of the 1:2 stoichiometric ratio required to form the zinc bis(diacetylene carboxylate), the blue image color will change to yellow at, or above, the same 100° C. temperature, but will revert to the original blue color when cooled below the transition temperature of 100° C.

By combining each of these embodiments (which generate, respectively, a blue or yellow color) in a separate integral layer, the combination of blue and yellow colors is complementary, thereby producing a black or neutral near black color. Similar mixtures utilizing lithium or magnesium in place of zinc have also shown similar superior imaging properties in producing permanent black or near black image colors.

As one of ordinary skill will readily recognize, the mole ratio of metal polyacetylene salt components or metal polyacetylene salt and non-metal polyacetylene salt components can vary widely depending upon their respective sensitivities in the mixtures provided for color balance. Generally, the mole ratio of one component to the other can vary between about 10:1 and about 1:10, more desirably between about 2:1 and about 1:2. Preferably, substantially equal amounts by weight of complementary colored crystals, e.g. blue and yellow, are provided in the present mixtures.

It is noted that with respect to the amount of a particular component to be included in compositions according to the present invention, the above-described mole ratios are to serve as a guide, not a limitation to the concentrations of the polyacetylenic compounds which may be included in the compositions. Other considerations such as the photosensitivity of the individual compounds, the overall color balance of the mixture as well as the color emitted and portion of the spectrum absorbed by the compound may also influence the concentration of polyacetylenic component chosen.

As mentioned above, the particular components of the present mixture are selected for their ability to develop images in complementary colors. The following are examples of colors which are considered complementary for purposes of this invention. Blue and yellow; magenta and green; cyan and red. Essentially, complementary colors are those which are chosen because of their ability to absorb a portion of the visible spectrum. In preferred embodiments, the mixture of complementary colors will absorb the entire spectrum of visible light, thus producing a black image color. One of ordinary skill may readily choose polyacetylenic compounds for inclusion in the present invention based upon the ability of photoproducts of the individual components to absorb portions of the visible spectrum such that the mixture will absorb substantially all of the visible light spectrum and produce a permanent black or near black image color.

Table I summarizes the metal salts of polyacetylene carboxylic acids which were tested for the purposes of this invention. The metal salt used as a standard in the Table, namely zinc bis(pentacosa-10,12-diynoate), has a photosensitivity of about 8 mJ/cm$^2$; which is almost twice the photosensitivity of pentacosa-10,12-diynoic acid. The zinc bis(pentacosa-10,12-diynoate) and the other metal salts in the following table were tested by applying an aqueous dispersion of the metal polyacetylene salt to a substrate in a thin layer of about 5 μm thickness, drying the dispersion and exposing the resulting coating to the 254 nm emission of a mercury arc lamp. The dispersions were prepared by mixing an aqueous gelatin solution and an aqueous solution of the sodium salt of the selected polyacetylene carboxylic acid before adding an aqueous zinc acetate solution at elevated temperature with mild agitation.

Another convenient method of comparing different polyacetylenes was to spot a single drop of a dispersion containing a standard amount of the polyacetylene metal salt on a filter paper which has a spot of zinc bis(pentacosa-10,12-diynoate) dispersion to act as a reference for comparison. In undertaking the above-described tests, it is particularly useful to use a consistent molar amount of the polyacetylene in preparing the dispersion, thereby obtaining a more accurate intercomparison of photosensitivities. It is particularly advantageous if the standard amount of the polyacetylene is selected from within the range of about 0.001 moles to about 0.5 moles per kilogram of dispersion. After the spots had dried, the filter paper was irradiated from a distance of about 4 ft with the 254 nm UV radiation of a mercury lamp. The 4 ft distance was used to obtain a substantially uniform exposure over the entire sample. As an exposure was being made, the spots were observed to darken. From the rate of darkening, the photosensitivities of the various diacetylene carboxylate metal salts were evaluated relative to the zinc bis(pentacosa-10,12-diynoate) reference. The colors of the spots were also observed and recorded. From the observations shown in the following table, it can be seen that the metal salts are most commonly about the same sensitivity as the parent diacetylene carboxylic acid except in the cases of lithium, zinc, manganese, rubidium and thulium where many of the metal salts are much more sensitive than the parent compounds.

| Metal Ion/ Cation | Color of Metal Diacetylenecarboxylates and Photosensitivity Relative to Zinc Bis(Pentacosa-10,12-Diynoate) | | | | | | | | | |
|---|---|---|---|---|---|---|---|---|---|---|
| | Diacetylenecarboxylate | | | | | | | | | |
| | A | B | C | D | E | F | G | H | I | J |
| H$^+$ | Blue/1 | — | Blue/1 | Blue/1 | 0 | — | Blue/1 | Blue/1 | Blue/1 | — |
| Li$^+$ | — | — | Dark red/3 | Red/4 | Blue/2 | — | Blue/2 | Blue/5 | — | Violet/1 |
| Mg$^{2+}$ | Pink/1 | Purple/2 | 0 | 0 | Purple/1 | Purple/1 | Blue/1 | Blue/1 | 0 | Blue/1 |
| Al$^{3+}$ | 0 | 0 | 0 | 0 | Blue/1 | Blue/1 | 0 | Blue/1 | 0 | Blue/1 |
| Ca$^{2+}$ | 0 | 0 | 0 | 0 | Blue/1 | Violet/1 | Blue/1 | Blue/2 | 0 | Blue/1 |
| Sc$^{3+}$ | 0 | 0 | 0 | 0 | 0 | Blue/1 | 0 | 0 | 0 | Blue/1 |
| Cr$^{3+}$ | Blue/1 | 0 | Blue/1 | Blue/1 | 0 | Blue/1 | Blue/1 | Blue/1 | 0 | 0 |
| Mn$^{2+}$ | Blue/2 | 0 | Pink/2 | Pink/2 | Purple/1 | Violet/4 | Violet/3 | Violet/4 | 0 | 0 |
| Fe$^{2+}$ | 0 | 0 | 0 | 0 | 0 | 0 | 0 | 0 | 0 | 0 |
| Co$^{2+}$ | 0 | 0 | Brown/1 | Brown/1 | 0 | 0 | 0 | 0 | 0 | 0 |
| Cu$^{2+}$ | 0 | 0 | 0 | 0 | 0 | 0 | 0 | 0 | 0 | 0 |
| Zn$^{2+}$ | Blue/3 | Blue/1 | Blue/3 | Blue/4 | Blue/3 | Blue/1 | Blue/3 | Blue/3 | 0 | Blue/1 |
| Rb$^+$ | Blue/2 | Blue/3 | Blue/1 | Blue/1 | Blue/1 | Blue/1 | Blue/1 | Blue/1 | Blue/1 | Blue/4 |
| Zr$^{4+}$ | Blue/1 | Blue/1 | Blue/3 | Blue/1 | Blue/1 | Blue/1 | Blue/1 | Blue/1 | 0 | Blue/1 |
| Mo$^{3+}$ | 0 | 0 | 0 | 0 | 0 | 0 | 0 | 0 | 0 | Blue/1 |
| Sn$^{4+}$ | Blue/2 | Blue/2 | Blue/2 | Blue/1 | Blue/1 | Blue/1 | Blue/1 | Blue/1 | Blue/1 | Blue/2 |
| Ba$^{2+}$ | Pink/1 | Pink/1 | Pink/1 | Blue/1 | Blue/1 | Blue/1 | Blue/1 | Blue/1 | 0 | Blue/1 |
| La$^{3+}$ | 0 | 0 | Purple/1 | Blue/1 | Blue/1 | Violet/1 | Blue/1 | Blue/1 | 0 | Blue/1 |
| Tm$^{3+}$ | Blue/2 | Blue/2 | Blue/2 | Blue/1 | Blue/1 | Blue/3 | Blue/1 | Blue/1 | 0 | Blue/2 |

A: Heptadeca-4,6-diynoic acid
B: Nonadeca-4,6-diynoic acid
C: Octadeca-5,7-diynoic acid
D: Eicosa-5,7-diynoic acid
E: Heneicosa-8,10-diynoic acid
F: Tricosa-8,10-diynoic acid
G: Tricosa-10,12-diynoic acid
H: Pentacosa-10,12-diynoic acid
I: Pentacosa-12,14-diynoic acid
J: Heptacosa-12,14-diynoic acid
Photosensitivity Scale (@ 254 nm):
0. No significant photosensitivity.
1. Much less photosensitive than zinc bis(pentacosa-10,12-diynoate)
2. Less photosensitive than zinc bis(pentacosa-10,12-diynoate)
3. Equal photosensitivity to zinc bis(pentacosa-10,12-diynoate)
4. More photosensitive than zinc bis(pentacosa-10,12-diynoate)
5. Much more photosensitive than zinc bis(pentacosa-10,12-diynoate)

Numerous metallic and non-metallic diacetylenic compounds may be used in the present invention. Preferred metallic and non-metallic diacetylenic compounds are those which produce complementary blue/yellow image colors. In general, in this mixture of complementary diacetylenic compounds, either a metallic or non-metallic polyacetylenic compound produces a blue or yellow color, such that the resulting combination of these complementary colors is the desired permanent black or near-black image color.

The polyacetylenic compounds which are included herein to provide a yellow image are those reported in U.S. Pat. Nos. 3,723,121; 4,705,742; 5,095,134; 5,139,927; 5,149,616; 5,149,617; 5,158,862; 5,215,869 and 5,215,870. Urethanyl polyacetylenic compounds described in U.S. Pat. No. 4,215,108, which provide golden and green-golden images, are also useful herein as a non-metal salt component of the present mixture. The disclosures of these patents are incorporated herein by reference. Other polyacetylenic compounds which provide non-yellow images are also incorporated herein as suitable non-metal components in complementary color combinations with a metal salt component.

In general, reactions based upon metal ion exchange between metals of the electromotive series, e.g. between a metal salt of a carboxylic acid and another salt of a second metal, are well known. Such reactions also apply to the preparation of the novel zinc salts of the present polyacetylene carboxylic acids.

For example, a particular method employed for the preparation of metallic salts of this invention involves reacting the polyacetylene $C_6$ to $C_{48}$ carboxylic acid, or a mixture thereof, with an aqueous solution of ammonia or the hydroxide of a Group I metal in the Periodic Table to produce the corresponding ammonium or Group I element salt of the $C_6$ to $C_{48}$ polyacetylene carboxylic acid. The resulting salt in aqueous solution is then reacted with an aqueous solution of a salt of another metal, e.g. Zn, selected to form the polyacetylene metal salt in an ion exchange reaction. The resulting metal salt of the polyacetylene carboxylic acid is either used directly or is recovered for use as a component in a mixture of the present invention. Where it is not intended to recover or separate the polyacetylene salt, but rather to use it directly, it is preferable to carry out the ion exchange reaction in the presence of an aqueous solution or dispersion of a binder. Preferred binders include gelatin, polymers and copolymers of vinyl pyrrolidone and acrylic polymers and copolymers containing acrylic acid residues.

Similar ion exchange reactions, substituting other ions for ammonium or Group I metal ions and/or substituting the zinc ion can be employed to produce the desired metal salt component of this invention by reference to the electromotive series of metals indicating metal ion replacement. In addition to the metal salt, e.g. zinc salt, of a diacetylene carboxylate, there is formed as a metal salt by-product, an ammonium or Group I metal salt in which the ammonium or Group I ion is combined with an anion which was initially a component of the original metal salt (e.g. zinc salt) reactant.

Generally, but not without exception, a metal salt reactant which is the metal salt of formic acid, or a secondary or tertiary alkyl carboxylic acid containing between 2 and 8 carbon atoms produce an acetylenic product which images to a red color when first exposed to radiation and subsequently heat treated; the metal salt reactants of linear alkyl carboxylate anions produce products imageable to yellow tones and hydroxy-substituted metal salt carboxylate reactants, e.g. $HO(CH_2)_3$—$COO^-$ give products imageable to magenta tones. In obtaining polyacetylene salts that produce a yellow color tone, it is particularly advantageous to conduct the exchange reaction between the sodium salt of a polyacetylene carboxylate and a metal salt of a linear alkyl carboxylate. These reactions should serve to guide, not limit, those of ordinary skill in producing chromogenic acetylenic compounds which may be used in the present invention.

Metal chloride reactants provide acetylenic compounds imageable to orange and metal sulfate and nitrate reactants produce acetylenic compounds imageable to blue. When a polyacetylene metal salt or a mixture of a polyacetylene metal salt with a non-metal salt is desired, a portion of the polyacetylene metal salt derivative consistent with the selected concentration for a desired color balance can be stripped of metal salt by-product by a plurality of water washes or a treatment with an ion exchange resin. The resulting portions can be obtained in situ or can be separately prepared and employed by individually mixing them prior to coating or coating each component as a discrete layer on a suitable substrate, e.g. a film base, glass plate, cellulose base, etc.

In a preferred aspect for preparing zinc salts according to the present invention, the sodium salt of a polyacetylene $C_6$ to $C_{48}$ carboxylic acid, more preferably a sodium salt of diacetylene $C_{14}$ to $C_{43}$ monocarboxylic acid is reacted in situ with the zinc salt of a $C_2$ to $C_8$ linear alkyl carboxylate (optionally, using zinc nitrate in substitution for or in addition to the zinc polycarboxylate) to form the respective zinc $C_6$ to $C_{48}$ polyacetylenic carboxylate. In forming the zinc $C_6$ to $C_{48}$ polyacetylenic carboxylate in situ, the resultant mixture, which contains the sodium salt of the $C_2$ to $C_8$ linear carboxylate and/or sodium nitrate as a by-product metal salt, will produce a yellow color after an initial photoexposure step followed by a thermal or heating step. This in situ preparation of the zinc polyacetylenic carboxylate is preferably used to generate a complementary yellow which will form a black image color in combination with a blue color by inherently incorporating an effective concentration of nitrate or carboxylate anion in combination with zinc diacetylenic carboxylate. An alternative to the in situ preparation of the mixture which produces a yellow color is a procedure employing any water soluble zinc salt which first produces the zinc $C_6$ to $C_{48}$ polyacetylenic carboxylate, then washes out by-product metal salt and the remaining zinc $C_6$ to $C_{48}$ polyacetylenic carboxylate species is combined with an effective concentration of the sodium salt of a linear alkyl carboxylate to produce a mixture imageable to a yellow color.

In a particularly preferred aspect of the present invention, the sodium salt of a polyacetylene $C_6$ to $C_{48}$ carboxylic acid, more preferably a sodium salt of a diacetylene $C_{14}$ to $C_{43}$ monocarboxylic acid, is reacted in situ with a mixture of zinc nitrate and the zinc salt of a $C_2$ to $C_8$ linear alkyl carboxylic acid to form the respective zinc diacetylene carboxylic acid. In forming this zinc diacetylene carboxylic acid in situ, the resultant mixture which contains sodium nitrate and sodium $C_2$ to $C_8$ linear alkyl carboxylate as by-product metal salts, will produce a black color after an initial photoexposure followed by a thermal heating step. This in situ preparation of the zinc acetylenic carboxylic acid is preferably used to generate compositions which will produce a black image color by inherently incorporating effective concentrations of sodium nitrate and sodium $C_2$ to $C_8$ linear alkyl carboxylate such that in combination with the zinc diacetylene carboxylate they will simultaneously yield blue and yellow complementary colors which add to form a black image color. The particular shade of black can be changed by altering the relative amounts of the nitrate and $C_2$ to $C_8$ linear alkyl carboxylate anions. An alternative to the in situ preparation of the mixture is a procedure which first produces the zinc diacetylene carboxylate, then washes out the by-product metal salts. The remaining zinc acetylene carboxylate is then combined with an effective concentration of sodium nitrate and an effective concentration of sodium $C_2$ to $C_8$ linear alkyl carboxylate to produce a mixture which provides blue and yellow colors simultaneously which together form a black color. In certain embodiments using this aspect of the present invention, the inclusion of a polyethyleneoxide containing additive (as described in more detail, hereinbelow) is advantageous.

In producing the compounds according to the present invention, several methods may be employed, all of which include mixing the polyacetylenic components in an effective amount of binder to stabilize the polyacetylenic components. Complementary polyacetylene components in crystalline form may be combined with binder and then used directly in that form or incorporated into or admixed with one or more film-forming polymers and used accordingly.

In addition, compositions according to the present invention which include a mixture of polyacetylenic compounds and binder may also include an amount of other compounds effective to instill the final composition with a proper or uniform color balance. It has been discovered unexpectedly that the inclusion of a compound containing a polyethyleneoxide or polypropyleneoxide moiety or chain provides the final composition with a favorable uniform color balance. Within this group of additives can be found the polyethyleneoxide polymers (including polyethyleneoxide/ polypropyleneglycol copolymers) of varying chain length (for example, having molecular weights ranging from about 200 to several hundred thousand or more, preferably having molecular weights ranging from about 500 to about 100,000, and being substituted or unsubstituted). Polypropyleneglycol polymers of varying molecular weight may also be used in the present invention in place of the polyethyleneoxide polymers. In addition, nonionic polyethyleneoxide containing surfactants, for example, one of the series of alkylphenolethoxylate surfactants (such as the Igepal™ surfactants such as Igepal CA-630, Igepal CO-990, Igepal CO-850, available from Rhone-Poulenc Corporation, or Triton X-100 available from Rohm & Haas, Inc., or a surfactant containing polyethyleneoxide/polypropyleneoxide copolymer chains, for example, poloxalene or the Pluronic™ or Polaxamer™ surfactants, such as Pluronic F68 and L62LF, Poloxamer 182LF, 188 or 331, available from a number of suppliers), may also be included to stabilize color formation in the present compositions. Other nonionic surfactants for use in the present compositions for this purpose include the polyethyleneoxide fatty alcohol ethers, for example, Alfonic ethoxylates, the BioSoft™ surfactants and Brij™, the polyoxyethyleneoxide fatty acid esters, such as Emerest 2600 series, among numerous others, including polyoxyethylene sorbitan monooleate (for example the Tween™ surfactants, among others). Numerous additional surfactants containing polyethyleoxide and/or polypropylene oxide chains may also be used in this aspect of the present invention.

The nonionic polyethyleneoxide or polypropyleneoxide containing additive is included in the present compositions which contain the polyacetylenic components and binder in amounts effective for instilling the final compositions with a uniform color balance. The additive is generally included in the final composition (which composition includes polyacetylene component and binder) in an amount ranging from about 0.01% to about 2%, more preferably about 0.05% to about 1% by weight of the composition, even more preferably about 0.1% to about 0.2% by weight. In certain embodiments according to the present invention, in particular, the embodiments wherein a zinc bis diacetylenic carboxylate compound is formulated in combination with a nitrate or linear alkyl carboxylate anion, the polyethyleneoxide containing additive, especially a surfactant of this type, may be included along with the nitrate or linear alkyl carboxylate anion, or may replace some or all of the linear alkyl carboxylate in producing effective compositions.

It is noted that in addition to the above ethyleneoxide or propyleneoxide containing additives and surfactants, other surfactants may also be included in the present compositions, for instilling the final compositions with uniformity and wettability when producing a final film using the present compositions. Virtually any surfactant known in the art to instill wetting characteristics to films may be added to the present compositions for this purpose. When a surfactant is used, it is generally added in an amount effective to provide a wetting character to the solutions containing polyacetylene compounds and binder which are deposited on substrates for use as films. The amount of surfactant commonly ranges from about 0.005% to about 1% by weight, more commonly about 0.05% to about 0.5% by weight.

Compositions according to the present invention comprise effective amounts of at least one polyacetylenic metal salt compound or at least one polyacetylenic metal salt compound and at least one non-metallic polyacetylenic compound which produce complementary colors upon exposure to radiant energy and/or thermal energy such that the resulting image is a permanent black or near black image color in combination with a binder. Compositions may optionally comprise a nonionic polyoxyethylene or polypropyleneoxide containing surfactant as well as other components such as film-formers and other additives.

Polyacetylene compounds of the present invention, in providing complementary colors to the final image, may be included in the same or multiple layers (ie., a laminate containing two or more layers). It will be understood that each individual color forming polyacetylene of the present color complementary mixtures can be contained in a separate layer of a laminate before imaging. Thus, for example, two polyacetylene compounds, which together produce one of the complementary colors can each form a layer and a third or separate layer may be employed for yet another metal salt or non-metal salt polyacetylene which is imageable to the color complement needed to produce the desired black image color.

In preparing compositions of the present invention, the polyacetylenic components in crystalline form may be admixed in the presence of a binder, preferably in the form of 1% to 30% aqueous solution in order to produce consistent formulations. For example, the selected crystalline components are prepared in an aqueous binder solution, dispersion or emulsion which contains, e.g., gelatin, polyvinylpyrrolidone, for example, K 15-K 90, vinylpyrrolidone copolymer, eg. poly(vinylpyrrolidone/alphabutene); or a (meth)acrylate polymer or copolymer (particularly, a polymer or copolymer of acrylic acid), each used alone or in admixtures, as a suspension, dispersion or emulsion. To the binder solution is added or formed in situ preferably about 1% to about 25 percent by weight, more preferably between about 4 % and about 15 percent by weight, solid microcrystals of the present polyacetylenic imageable components. One of ordinary skill in the art will readily recognize to modify the concentrations of binder and polyacetylene compound(s) in solution in order to produce a final composition containing the desired weight ratios of binder to polyacetylene compound(s). Such a method is described in, for example, U.S. Pat. No. 4,784,934. Surfactants may also be added in appropriate amounts along with other additives such as film-forming polymers (other than the binders which may themselves have certain film-forming characteristics), stabilizers, viscosity modifiers such as thickeners, etc.

Replacing the gelatin in whole or in part with vinyl pyrrolidone polymers or copolymers provides longer lasting thermal desensitization of the diacetylene component. The resulting product(s) either as mixed or separate aqueous mixtures can then be applied to any flexible or inflexible substrate or support, including, for example, a film base, paper, glass, etc. in one or more layers by any conventional method including extrusion, cascade coating, slot coating, spin coating, roll coating, curtain coating and spray coating techniques. Film bases which are generally used in the art as a support in films include, for example, polyethylene, polypropylene or polyester films, other plastics and resins, paper alone or coated with plastics such as polyethylene and polyvinylchloride, among numerous others well known in the art. It is preferable that the film base have a melting temperature greater than the treatment temperature employed to produce the black or neutral near black color.

Layer thicknesses of the polyacetylene components on the film base between about 0.2 and about 50 μm, more preferably between about 0.5 and about 10 μm, are recommended. The particular layer thickness of individually coated components can be somewhat modified to accommodate differences in photosensitivity between individual photosensitive components which are imageable to a different color. The layer of the less active photosensitive component is generally applied in a relatively thicker and/or denser coating to achieve desired color balance.

It will be understood that each individual color forming polyacetylene of the present color complementary mixtures can be contained in a separate layer before imaging. Thus, for example, two metal salt diacetylene carboxylic acids, which together produce one of the complementary colors can each form a layer and a third or separate layer can be employed for another metal salt or non-metal salt diacetylene which is imageable to the color complement needed to produce the desired black image color. These layers may be adjacent to one another, or separated by one or more intervening layers. Layers may be formed simultaneously, sequentially, or by laminating together two or more separate layers.

The compositions may be used in the presence of a film-forming polymer in order to produce polymeric films, however it must be recognized that the film-forming polymer may absorb some of the radiant energy used for development of color. Care must be taken to select a film-forming polymer in order to minimize its energy-absorbing effect so as not to complicate the color development process.

The development of complementary colors in the imaging of colorless crystalline metal salt and non metal salt polyacetylenic components useful for this invention can be accomplished by several methods. For example, the aqueous mixture or mixtures can be directly exposed to high energy, e.g. radiation having an effective wavelength below about 400 nm. Sources of exposure include radiation generated from an electron beam, a mercury xenon arc lamp, a mercury arc lamp, a xenon flash lamp, actinic light, neutrons, X-rays, gamma rays, beta rays, alpha particles, electron corona discharge, or a UV laser capable of polymerizing the crystalline photosensitive polyacetylenic component(s) to the corresponding imageable homopolymer(s); thus creating a positive, visible colored reproduction of the image being transmitted.

In another aspect of the present invention, the composite mixture or layers of individual components can be first heated to a decomposition temperature at which the photoactivity of the crystalline acetylenic component exposed to the heat is destroyed. Preferably this temperature is between about 50° and about 200° C. more commonly between about 70° and about 130° C. Attainment of this temperature for about 1 microsecond or more results in the formation of an invisible, latent reproduction of the image being transmitted. This heat exposed mixture is then subjected to the previously discussed high energy radiation whereupon color develops in the non-heated portions of the mixture owing to the polymerization of the residual photoactive polyacetylene component.

After exposure by either of the above methods, the impinged products are subjected to a final thermal treatment to develop a temperature between about 50° C. and 200° C., more preferably about 100° C. and about 150° C. The heat treatment which produces a permanent black image color is generally performed for a period of at least about 1 microsecond, more commonly at least 0.01 second, even more commonly within a range of about 0.01 to about 10 seconds. By means of this exposure to heat, at least a portion of the polymerized, color forming diacetylene mixture undergoes an irreversible thermochromic transition.

By judicious selection of polyacetylene combinations, the thermal treatment involves forming a balanced proportion of the two complementary colors which produce the neutral black or near black image color. Thermal energy exposure may be generated by conventional means such as by a heated roller, platen or plate. Alternatively, the heating means may be an intense light exposure which, by absorption in the layer or adjacent layer, heats the mixture to annealing temperature and forms a permanent change. This temperature generally ranges from about 50° C. to about 200° C., more preferably about 100° C. to about 150° C.

Alternatively, a laser transmitting energy at a longer wavelength, for example above about 700 nm up to about 1,500 nm or higher can be employed, provided that a suitable energy absorbing, heat transmitting component, (e.g. an energy absorbing polycarbocyanine, pyrylium, squarilium dye, or dye mixtures or dye intermixtures, etc.) is used in conjunction with the metal salt component mixture to absorb energy from the laser and to transmit sufficient heat to the homopolymer so that a permanent latent image or pattern is transmitted. The energy absorbing, heat transmitting agent is one having absorption capability in a wavelength similar to the transmitting laser and is capable of raising the temperature of the homopolymer to between 50° C. and 500° C., preferably between about 100° C. and about 150° C. When an energy absorbing dye is employed, the weight ratio of homopolymer to dye can vary between about 1000:1 and about 1:10, depending upon the amount of homopolymer present and the amount of radiation energy needed to be converted to heat energy. Most often the dye comprises between about 0.005 and about 1% by weight of the active imaging component.

The polyacetylene salt dyes suitable for absorbing energy at wavelengths of 575 nm or higher and their preparation is disclosed in U.S. Pat. Nos. 5,153,106; 5,137,964 and 5,232,820 the teachings of which are incorporated herein by reference. These polyacetylene salt dyes are suitable as a component in the present mixtures providing the complementary colors. Suitable lasers for this final, high energy exposure include GaAlAs, NaYtAl garnet, ruby, NaYAg, Ar, He-Ne, He-Cd, GaAs NeYAl garnet, NaYAg, krypton ion, copper vapor lasers, etc.

Accordingly, crystalline, gas, liquid dye or amorphous solid, pulsed or continuous wave lasers can be used which transmit temperatures in about the 110°–160° C. range sufficient to induce a thermochromic, permanent color change in the laser exposed areas of the acetylenic mixtures.

Having generally described the invention, reference is now made to the following examples intended to illustrate preferred embodiments and comparisons but which are not to be construed as limiting to the scope of this invention as more broadly set forth above and in the appended claims.

EXAMPLE 1

Control Dispersion of Pentacosa-10,12-Diynoic Acid in Gelatin

The following solutions were prepared:
Part A 5 g. of gelatin and 0.1 g. of Alkanol-XC* were dissolved in 110 g. of deionized water at 50° C.

* dupont tradename for sodium alkyl naphthalene sulfonate

Part B

Pentacosa-10,12-diynoic acid (5 g.) was dissolved in 5 g. of n-butanol at 50° C.

To prepare the dispersion, Part A was heated to 75° C. and agitated at high speed with a mixer-emulsifier throughout the addition of Part B. After 5 minutes of mixing, the agitation was stopped and the mixture was chill set at about 4° C., cut into cubes about 1 cm in size and vacuum dried to remove approximately 85% of the n-butanol. This dispersion product was reconstituted by melting at 50° C. and adding deionized water to replace the liquids lost in the drying process. Finally the dispersion was ripened by adding 9% by weight of methanol and agitating slowly at 50° C. for 1 hour. The dispersion was chill set and refrigerated for storage.

EXAMPLE 2

Preparation of a Dispersion of Zinc Bis(Pentacosa-10,12-Diyonate) in Gelatin

The following solutions were prepared:
Part A 5 g. of a lime-bone gelatin was swelled and dissolved in 20 g. of deionized water.

Part B 5 g. (0.0134 moles) of pentacosa-10,12-diynoic acid was dissolved in 13.4 ml of 1N sodium hydroxide and 65 g. of deionized water at 70° C.

Part C 1.46 g. (0.0067 moles) of zinc acetate dihydrate was dissolved in deionized water to form a 0.5 molar solution.

To prepare a dispersion of zinc bis(pentacosa-10,12-diynoate), Part A and Part B were mixed at 50° C. forming a viscous solution. While the resulting solution was being agitated, Part C (at 50° C.) was added directly into the mixing zone. The viscosity of the resulting mixture rapidly decreased and the mixture slowly became opaque as a dispersion of zinc bis(pentacosa-10,12-diynoate) particles developed in the gelatin solution. After the addition of Part C, the dispersion was kept at 50° C. and from time to time small quantities of dispersion were removed and spotted onto filter paper. When these spots were subsequently exposed to the 254 nm emission of a mercury lamp, they turned bright blue. From the depth of the color developed when the dispersion spots were given equal amounts of UV exposure, it was evident that the photosensitivity of the dispersion increased rapidly in the first 10 minutes after mixing, and asymptoted to a consistent high value after about 30 minutes.

When a spot of the zinc salt dispersion and a spot of the Control Dispersion of Example 1 were placed side-by-side on filter paper and given equal exposures with the 254 nm emission of a mercury lamp, the zinc salt dispersion developed a blue color far more rapidly than the control sample. In fact it took more than twice as long to develop the same depth of color in the Control Dispersion. From this observation it was inferred that the zinc salt dispersion was at least twice as photosensitive as the Control Dispersion.

The zinc salt dispersion can be chill set and stored under refrigeration.

EXAMPLE 3

Dispersion of the Zinc Salt of Nonadeca-4,6-Diynoic Acid

The method of Example 2 was used to prepare this dispersion, except that Part B contained 5 g. (0.0172 moles) of nonadeca-4,6-diynoic acid and 17.2 ml of 1N sodium hydroxide and Part C contained 1.89 g. (0.0086 moles) of zinc acetate dihydrate. After Parts A, B and C had been mixed to prepare a dispersion of zinc bis(nonadeca-4,6-diynoate), a small quantity of the dispersion was withdrawn at various time intervals and spotted onto filter paper. When the spots were exposed to a 254 nm UV light source, it was evident that full photosensitivity of the dispersion does not develop until about 10–15 minutes after mixing.

When spots of the dispersions of this Example and Example 2 were placed side-by-side on filter paper and exposed to 254 nm UV radiation, a slightly greater amount of blue color developed with the latter dispersion indicating that it was the more photosensitive of the two.

EXAMPLE 4

Dispersion of the Zinc Salt of Eicosa-5,7-Diynoic Acid

The method of Example 2 was used to prepare this dispersion, except that Part B contained 5 g. (0.0164 moles) of eicosa-5,7-diynoic acid and 16.4 ml of 1N sodium hydroxide and Part C was made with 1.81 g. (0.00825 moles) of zinc acetate dihydrate.

When spots of this dispersion and the dispersion of Example 2 were placed side-by-side on filter paper and exposed to 254 nm UV light, the dispersion made with eicosa-5,7-diynoic acid developed greater blue coloration indicating that it was the more photosensitive of the two.

EXAMPLE 5

Dispersion of the Lithium Salt of Pentacosa-10,12-Diynoic Acid

This dispersion was made by the method of Example 2 except that Part C contained 0.568 g. (0.0134 moles) of lithium chloride dissolved in deionized water to form a 1M solution.

After Parts A, B and C were mixed, a dispersion of lithium pentacosa-10,12-diynoate developed over several minutes. Maximum sensitivity to 254 nm UV radiation developed in about 10–15 minutes. When a spot of the dispersion of this Example was placed side-by-side on filter paper with a spot of the dispersion of Example 2 and the spots were exposed to 254 nm UV radiation, both spots develop a dark blue color, but it took much longer exposure of the zinc salt of Example 2 to develop the same depth of color. This indicates that the lithium salt of this Example was more photosensitive than the zinc salt. By estimation, it was observed that the lithium salt dispersion was at least 10 times more photosensitive.

EXAMPLE 6

Dispersion of the Lithium Salt of Eicosa-5,7-Diynoic Acid

This dispersion was made by the method of Example 2 except that Part B contained 5 g. (0.0164 moles) of eicosa-5,7-diynoic acid and 16.4 ml of 1N sodium hydroxide and Part C contained 0.695 g. (0.0164 moles) of lithium chloride dissolved in water to form a 1M solution. After mixing Parts A, B and C, the dispersion formed slowly over a period of several hours. When spots of the dispersion were dropped onto filter paper and exposed to UV light, the sensitivity was low immediately after mixing, but increased to a maximum after several hours. In contrast to all the previous Examples 1–5, the photoproduct of this dispersion was bright red rather than blue. This color difference made it less easy to compare the photosensitivity with the other dispersions. Notwithstanding, during UV exposure, coloration of this dispersion developed more rapidly than the dispersion of Example 2. This indicated that the lithium dispersion of this Example was the more sensitive of the two.

EXAMPLE 7

Coatings of Dispersion Samples 10 g. aliquots of the dispersions of Examples 1–6 were melted at 40° C. whereupon 0.425 g. of a 10% aqueous solution of Triton X-100 surfactant** was mixed with each sample. Samples were then coated on polyester film base using a doctor blade with a 0.006 inch coating gap. Coatings were chill set and dried. The thickness of the dry, coated layers was measured to be about 8 μm. When these coatings were exposed to 254 nm UV radiation, the lithium pentacosa-10,12-diynoate dispersion was observed to be the most sensitive followed by lithium eicosa-5,7-diynoate. The zinc salts of pentacosa-10,12-diynoic acid, eicosa-5,7-diynoic acid and nonadeca-4,6-diynoic acid were of similar photosensitivity, but less sensitive than either of the lithium salts. All the diacetylene metal salt dispersions were more sensitive than the pentacosa-10,12-diynoic acid dispersion of Example 1.

** TRITON X-100 is a non-ionic surfactant made by Rohm and Haas.

Exposed areas of all the coatings were observed under 500x magnification. From this it was apparent that all coatings exhibited excellent clarity and very low granularity. This observation is consistent with the size of the dispersion particles being substantially less than 1 μm in size.

EXAMPLE 8

Visible Absorption Spectra

The coatings of Example 7 were exposed to 254 nm UV radiation sufficient to develop a visual absorption density of about 1.0 du.

The absorption spectra of the colored photoproducts were measured on a spectrophotometer with the following results:

| Absorption Maxima | | |
|---|---|---|
| Example | Active Component | nm |
| 1 | Pentacosa-10,12-diynoic acid | 655 |
| 2 | Zinc bis(pentacosa-10,12-diynoate) | 635 |
| 3 | Zinc bis(nonadeca-4,6-diynoate) | 650 |
| 4 | Zinc bis(eicosa-5,7-diynoate) | 655 |
| 5 | Lithium pentacosa-10,12-diynoate | 660 |
| 6 | Lithium eicosa-5,7-diynoate | 560 |
| 7 | Zinc bis(octadeca-5,7-diynoate) | 665 |

EXAMPLE 9

Diacetylenecarboxylate Metal Salts

The following steps are representative of the general method by which metal salts of diacetylene-carboxylates can be made.

5 g. of a 0.01 molar aqueous solution of sodium pentacosa-10,12-diynoate is warmed to 50° C. and rapidly mixed with 2.5 g. of a 0.01M aqueous solution of zinc acetate dihydrate. The zinc diacetylenecarboxylate salt precipitates immediately. With other monobasic diacetylenecarboxylic acids a 5 g. portion of a 0.01 molar solution of the diacetylenecarboxylate is used. For dibasic acids, 2.5 g. of a 0.01 molar solution of the diacetylenecarboxylate is used. When other metal salts or cations are used, different amounts of the 0.1 molar aqueous solutions of these salts are used as follows:

| For monovalent metal ions or cations | : 5 g. |
|---|---|
| For divalent metal ions or cations | : 2.5 g. |
| For trivalent metal ions or cations | : 1.67 g. |
| For quadrivalent metal ions or cations | : 1.25 g. |

EXAMPLE 10

Thermochromic Properties of Pentacosa-10,12-Diynoic Acid

Using the method of Example 7, a coating was made of the pentacosa-10,12-diynoic acid dispersion of Example 1. Exposure of this coating with 254 nm UV light led to the characteristic formation of a blue color which is the result of polymerization of the diacetylene.

When this blue film was run over a hot roller at about 75° C. for about 5 seconds the blue color changed instantly and irreversibly to a red color. The red color persisted when the film was cooled to ambient temperature (20° C.–25° C.), or even when the film was chilled in liquid nitrogen. Substantially the same blue to red color change occurred at roller temperatures up to about 150° C. However, when the film was heated to between about 150° C. and 200° C. the initial color change was from blue to yellow. Then, as the film was cooled below about 150° C., the yellow color was slowly replaced by the same permanent red color described above.

When absorption spectra of the blue and red films were obtained, it was evident that the heat treatment caused the absorption bands in the blue film to shift about 100 nm to lower wavelength in the red film. When the blue and red films were overlaid a purple color resulted.

EXAMPLE 11

Thermochromic Properties of Zinc Bis(Pentacosa-10,12-Diynoate) Dispersion

Using the method of Example 7, a coating was made of the zinc bis(pentacosa-10,12-diynoate) dispersion of Example 2. When this coating was exposed to 254 nm UV radiation a characteristic blue color quickly developed owing to the polymerization of the diacetylene.

The blue film was then passed over a hot roller at between about 105° C. and 150° C. for about 6 seconds, and unexpectedly the color changed immediately to an orange-yellow. This color change was permanent and persisted down to at least liquid nitrogen temperature. When the absorption spectra of the blue and orange-yellow colors were obtained, it was found that the two absorption bands at about 635 nm and 580 nm in the blue film had merged to form a single band at about 495 nm in the orange-yellow film. When the blue film was overlaid with the orange-yellow film, a black image color resulted.

Example 2 describes the use of sodium hydroxide in preparing the dispersion. If dispersions are made instead with ammonium hydroxide, tetraethylammonium hydroxide, potassium hydroxide, rubidium hydroxide or cesium hydroxide, the blue to orange-yellow color change does not occur, but instead a blue to red-orange color change takes place.

Also, if when using sodium hydroxide as described in Example 2, the lime-bone gelatin is replaced by an acid process porkskin gelatin, or by other water soluble binders including polyvinylpyrrolidone, GANEX*P-904, GAFQUAT*755N, polyvinylpyrrolidone-vinyl acetate copolymer, poly(sodium acrylate) and polyacrylamide, the blue to orange-yellow color change is observed, as previously described. However, if a phthalated bone gelatin is used, the color change is from blue to red-orange.

* Trademark of ISP

EXAMPLE 12

Washing the Zinc Bis (Pentacosa-10,12-Diynoate) Dispersion of Example 2 and the Thermochromic Properties Thereof A 100 g. sample of the dispersion of Example 2 was prepared, chill set at 4° C. and cut up into about 1 cm pieces. The dispersion pieces were soaked in about 1 liter portions of deionized water at 4° C. for at least 4 hours. The deionized water was drained and replenished twice, each time at least 4 hours was allowed for soaking. Finally the dispersion was drained. During the washing process, water soluble ions (e.g. $Na^+$, $Zn^{2+}$, acetate) are removed from the dispersion.

The washed and drained dispersion was melted at 40° C. and about 5 g of a 10% aqueous solution of TRITON X-100 was added as a coating aid. Portions of the dispersion were then coated onto polyester film base using a doctor blade with a 0.006" gap. When dried, these coatings had a thickness of about 8 µm. The coatings were then exposed to 254 nm UV radiation whereupon they rapidly turned deep blue.

The photoreactivity and subsequent blue color of the coatings of washed dispersion were indistinguishable from the photoreactivity and color of the unwashed dispersion of Example 2. However, when the blue colored film from the washed dispersion was heated at temperatures between about 105° C. and 130° C. an initial change to a magenta color was noted. Moreover, the magenta color was found to be not permanent, and when the film was cooled to temperatures below about 90° C. the original blue color returned. This same reversible color change was observed when the heating-cooling cycle was repeated many times. This behavior contrasts with the performance of the unwashed dispersion of Example 11 and demonstrates that the agent responsible for the orange-yellow color formation of Example 11, has been removed.

EXAMPLE 13

Addition of Metal Salts to the Washed Dispersion of Example 12

5 g. aliquots of the washed dispersion of Example 12 (including the TRITON X-100 coating aid) were warmed to 40° C. Approximately 0.6 g of 1M sodium chloride, 1M potassium chloride, 1M sodium acetate, 0.5M zinc acetate, 0.5M calcium chloride, 0.33M lanthanum chloride and 0.25M zirconium sulfate were added to separate dispersion samples and the samples were coated onto a polyester film base with a 0.006" doctor blade.

All coatings, when exposed to 254 nm UV, photopolymerized to yield the same characteristic blue color. The photosensitivity of the samples was substantially the same. However, when the blue films were heated to 105° C.–130° C. and cooled to ambient temperature (20° C.–25° C.), differences were observed as indicated in the following table:

| | Thermochromic Changes | | |
|---|---|---|---|
| Additive | Initial color (ambient temp[1]) | Color at 105–125° C.. | Final color at ambient temp[1] |
| Sodium chloride | blue | orange-yellow | red-orange |
| Potassium chloride | blue | orange-yellow | red-orange |
| Sodium acetate | blue | yellow | orange-yellow |
| Zinc acetate | blue | magenta | blue |
| Calcium chloride | blue | orange-yellow | red |
| Lanthanum chloride | blue | orange-yellow | red-orange |
| Zirconium sulfate | blue | orange-yellow | red |

[1] Ambient temperature was 20° C.–25° C.

From these observations it was deduced that in order to obtain a final color closest to yellow, both sodium ions and acetate ions are advantageously present. The presence of either ion alone was insufficient in this experiment to generate this color. Furthermore, it was observed that with lesser amounts of any of the additives the color change behavior tended towards the reversible behavior observed for the washed dispersion itself, i.e. blue to magenta to blue. On the other hand, with larger amounts of sodium chloride, potassium chloride, calcium chloride, magnesium chloride, lanthanum chloride or zirconium sulfate the behavior tended towards color changes of blue to orange-red (at 105° C.–130° C.) to red (upon cooling to ambient temperature of 20° C.–25° C.)

EXAMPLE 14

Addition of Zinc Salts to the Zinc Bis(Pentacosa-10,12 Diynoate) Dispersion of Example 2

10 g. of the washed zinc bis(pentacosa-10,12-diynoate) dispersion of Example 12 was melted at 40° C. and 0.25 g. of a 10% aqueous solution of Triton X-100 surfactant was added. Thereafter, approximately 1.3 g. of a 0.5M solution of zinc acetate dihydrate was added and the mixture was coated on a polyester film base using a doctor blade with 0.006" gap. The coating was chill set and dried.

When the coating was exposed to 254 nm UV radiation it rapidly developed the characteristic blue color described in previous Examples. However, when this blue film was passed over a hot roller at 110° C. for 5 seconds it did not irreversibly change from blue to orange-yellow as described in Example 11, but instead followed the behavior described for the washed dispersion of Example 12, returning to a blue color as the film cooled to the ambient temperature of 20° C.–25° C. This demonstrated that the presence of excess zinc ion suppresses the irreversible thermochromic color changes.

EXAMPLE 15

Temperature Dependance of Thermochromic Changes of the Zinc Bis(Pentacosa-10,12-Diynoate) of Example 2 and Neutral Color Formation It is described in Example 11 that upon exposure of a film containing zinc bis(pentacosa-10,12-diynoate) to 254 nm radiation, the film turns a blue color. Furthermore, when this blue colored film is heated above about 110° C. and subsequently cools to 20° C.–25° C., an irreversible change to an orange-yellow color occurs.

However, it was also observed that other irreversible color changes occur when the blue film was heated to temperatures in the range from about 75° C. to about 105° C., before cooling to ambient temperature of about 20° C. to 25° C. Inspection of heat treated film samples indicated that the blue image color changed to a more neutral color as would be obtained by a mixture of orange-yellow and blue colors. The color balance changed with increase in treatment temperature as evidenced by the increase in the ratio of orange-yellow: blue colors. The effect was such that with a 90° C.–100° C. treatment temperature, the film sample took on a neutral color balance and appeared grey-black when it had cooled to ambient temperature. This indicated that a neutral colored image could be made using a single layer of the zinc bis(pentacosa-10,12-diynoate) imaging component.

A further observation was made that with addition of sodium acetate to the dispersion, the coatings showed modified thermochromic behavior in that the orange-yellow image color became more prevalent at equivalent treatment temperatures.

EXAMPLE 16

Step Tablets and Neutral Color Formation

Using the procedure of Example 7 coatings of non-washed (Example 2) and washed (Example 12) dispersions of zinc bis(pentacosa-10,12-diynoate) were prepared. 1"×8" strips cut from each coating were placed side-by-side and exposed with 254 nm UV light to create exposure step-tablets. The exposure times for adjacent steps on the tablets were related by a factor of approximately the square root of 2 ($\sqrt{2}$).

Initially the step-tablets were both blue and exhibited similar visual densities on corresponding steps. The result of overlaying the step-tablets was a blue composite tablet. Both the step tablets were then passed over a hot roller at 110° C. for about 5 seconds whereupon the tablet made from the non-washed dispersion coating turned bright orange-yellow and the tablet made from the washed dispersion remained blue. When these step tablets were overlaid and observed in transmitted light, the result was a composite step-tablet with a neutral grey-black color.

EXAMPLE 17

Dispersions made with Zinc Bis(Nnondeca-4,6-Diynoate) and Zinc Bis(Eicosa-5,7-Diynoate)

Dispersions of the zinc salts of nonadeca-4,6-diynoic acid and eicosa-5,7-diynoic acid are described in Examples 3 and 4 respectively. When these dispersions are separately coated using the procedure of Example 7 and subsequently exposed to 254 nm UV light they rapidly turn blue. When these blue films are heated briefly to about 110° C. and cooled to 20° C.–25° C. they undergo irreversible color changes from blue to yellow. This contrasts with zinc bis(pentacosa-10,12-diynoate), which turns orange-yellow as described in Example 11.

When the zinc bis(nonadeca-4,6-diynoate) and zinc bis (eicosa-5,7-diynoate) dispersions were washed as described for zinc bis(pentacosa-10,12-diynoate) in Example 12, they both showed the same behavior in that, after exposure to form a blue photoproduct, they undergo no irreversible color changes when heated to 110° C. and maintain the blue color upon returning to the ambient temperature of 20° C.–25° C.

EXAMPLE 18

Preparation of a Dispersion of the Barium Salt of Docosa-10,12-Diyndioic Acid

The method of Example 2 was used to prepare this dispersion, except that Part B contained 5 g (0.0138 moles) of docosa-10,12-diyndioic acid and 27.6 ml of 1N sodium hydroxide and Part C was made with 3.52 g (0.0138 moles) of barium acetate.

When spots of this dispersion and the dispersion of example 2 were placed side-by-side on filter paper and exposed to 254 nm UV light, the dispersion made with pentacosa-10,12-diynoic acid developed greater coloration indicating that it was the more photosensitive of the two. In fact, the dispersion of example 2 was much more photosensitive than the dispersion of this example. Also, the barium salt, even after exhaustive irradiation, produced a plum-colored polymer, not the black color published in *Die Makromoleculare Chemie*, 154,35–48 (1972).

EXAMPLE 19

Preparation of a Dispersion of Docosa-10, 12-Diyndioic Acid

The method of example 18 was used to prepare this dispersion, except that Part C contained 27.6 ml of 1N sulfuric acid. When spots of this dispersion and the dispersion of example 2 were placed side-by-side on filter paper and exposed to 254 nm UV light, the dispersion made with pentacosa-10,12-diynoic acid developed greater blue coloration indicating that it was the more sensitive of the two. The photosensitivity of this dispersion was much less than that of example 2. After exhaustive irradiation, a pale blue color polymer was produced, which contrasts with the blue-black color published in *Die Makromoleculare Chemie*, 154, 35–48 (1972).

EXAMPLE 20

Thermochromic Properties of a Dispersion of Docosa-10,12-Diyndioic Acid and of its Barium Salt Coatings of dispersions of Examples 18 and 19 were made by following the method in example 7. Thermochromic properties were evaluated by first exposing the coatings to 254 nm UV light, which produced blue color, and then by heating the exposed coatings (100°–150° C.) for about 8 seconds. Coatings of both examples 18 and 19 did not show any non-reversible thermochromic properties.

EXAMPLE 21

Dispersion of Zinc Bis(Eicosa-5,7-Diynoate) in Gelatin made with a Mixture of Zinc Acetate Dihydrate and Zinc Nitrate Hexahydrate The method of Example 4 was used to prepare this dispersion, except that Part C contained 1.20 g (0.00545 moles) of zinc acetate dihydrate and 0.82 g (0.00274 moles) of zinc nitrate hexahydrate dissolved in 10.5 g of deionized water such that the molar ratio of zinc acetate dihydrate to zinc nitrate hexahydrate was 2:1.

This process eliminates the need for making two types of dispersion—one that would give the blue color (either by washing a dispersion, as in Example 12, or by adding appropriate metal salt, as in Example 13) and the other that would give the complementary yellow color (as in Example 13) to produce the neutral black image color (described in Example 16).

EXAMPLE 22

Thermochromic Properties of Zinc Bis(Eicosa-5,7-Diyonate) made with a Mixture of Zinc Acetate Dihydrate and Zinc Nitrate Hexahydrate Using the method of Example 7, a coating was made of the zinc bis (eicosa-5,7-diyonate) dispersion of Example 21. When this coating was exposed to 254 nm UV radiation, a characteristic blue color developed as a result of the formation of polydiacetylene. The blue film was then heated to 110° C. and the result was a neutral grey-black image color.

Thus, from a single dispersion made from one diacetylene and a single layer of coating, a neutral black film can be obtained.

EXAMPLE 23

Triton X-100: an Aid for Both Coatability and Color Balance

Triton X-100 is used as a coating aid as described in Example 7. Substitution of another surfactant viz. FC-129*[1] for Triton X-100 improved the coatability of the dispersions because the fluorochemical surfactant is more active towards reducing surface tension of the dispersion.

*[1]: FC-129 and FC-135 are fluorochemical surfactants made by 3M Co.

Surprisingly, when this substitution is made with the dispersion of Example 21 it affected the thermochromic properties of the dispersion. Exposure to 254 nm UV radiation produced blue polydiacetylene. Heat treatment, however, produced a green-black image color instead of the more neutral grey-black image color obtained when Triton X-100 was used.

This finding was confirmed by extending the substitution of surfactants similar in chemical composition, to both FC-129 and Triton X-100. FC-135, Igepal CA-630, Igepal CO-990 and Igepal CO-850 were tested. FC-135, similar in chemical composition to FC-129, gave similar results while the Igepal*[2] series, chemically similar to Triton X-100, had the same effect on thermochromism as Triton X-100. This indicates the importance of Triton X-100 not only as a coating aid but also as an aid to proper color balance.

*[2]: Igepal surfactants are non-ionic, ethoxylated alkyl phenols. Igepal is a trademark of Rhone-Poulenc Corporation.

EXAMPLE 24

Zinc Propionate: An Important Additive for Color Balance

Dispersions are ripened to increase their sensitivity to UV radiation by the methods described in Example 29. It was determined that neutralization of the excess sodium salt of 5,7-eicosadiynoic acid by an equimolar amount of zinc propionate was better with respect to the thermochromic properties of the film than when the neutralization was done by using zinc acetate, zinc formate or zinc nitrate. Neutralization with zinc propionate produced a better neutral black color balance as evidenced by the equal absorption of red, green and blue light.

EXAMPLE 25

Neutral Color Formation: Mixture of Ripened and Unripened Dispersions

Dispersion of zinc bis(eicosa-5,7-diyonate) was prepared according to Example 4. Part of this dispersion was ripened as described in Example 29 and then washed according to Example 12. The rest was left unripened and unwashed. An 8 μm thick coating of the washed and ripened protion had a photosensitivity of about 2 mj/cm$^2$ (UV exposure at 254 nm required to produce visual density of 2.0). UV exposure produced a blue image which remained blue even after thermal treatment at 110° C. Similar coating made from the unwashed and unripened portion had a photosensitivity of about 13 mj/cm$^2$. This sample had an initial color of blue when exposed to UV radiation and a thermochromic change to bright yellow when heated to 110° C.

1.5 g of the unripened dispersion was combined with 1.0 g of ripened dispersion and coated as described in Example 7. 254 nm UV radiation produced a blue image which turned to neutral black when heat treated at 110° C. The photosensitivity of the mixture was determined to be 10 mj/cm$^2$. Triton X-100 was found to be an important ingredient for desirable thermochromic properties (as in Example 23). Microscopic evaluation of the coatings indicated that the coatings made from dispersion in Example 21 had better clarity and granularity than the mixture in this Example.

EXAMPLE 26

Neutral Color Development: Processing Temperature and Time

A film coating of the zinc bis(eicosa-5,7-diynoate) dispersion (Example 29) turns blue when exposed to 254 nm UV radiation. The final color achieved after heat treating the film is dependant upon the processing temperature. At temperatures lower than the optimum, a slightly blue tone is seen in the high density regions, and at too high a processing temperature the low density regions appear slightly pink. The result is dependant upon the actual temperature attained in the imaging layer. For a coating of 8 μm thickness, the temperature of 110°–115° C. is sufficient to produce the neutral black color.

EXAMPLE 27

Desensitization or Fixation of the Image

A coating of zinc bis(eicosa-5,7-diynoate) was made as described in Example 29. It was masked with a simple pattern and exposed to 254 nm UV radiation. Those areas that were not masked turned blue. The mask was then removed and the film processed as described in Example 15. The blue areas turned neutral black while the masked, unexposed areas remained white/clear. The processed film with the image was exposed to additional 254 nm UV radiation. However, there was no density changes in either the neutral black or the clear regions indicating that the image was fixed and that the unexposed diacetylene metal salt had been desensitized.

EXAMPLE 28

Processing does not Affect Resolution

Using the procedure describe in Example 27, a line pattern was made on a film of zinc bis(eicosa-5,7-diynoate).

The line pattern consisted of 0.75 μm wide lines with 0.75 μm wide spacings. The exposed areas turned blue, while the unexposed areas remained clear. One such image was processed as described in Example 15 to produce the neutral black image color. Comparative microscopic analysis of processed (neutral) and unprocessed (blue) images showed that processing had not affected the resolving power of the film.

EXAMPLE 29

Preparation and Ripening of a Dispersion of Zinc-Bis (Eicosa-5,7-Diyonate)

40 g of a lime-bone gelatin was swelled and dissolved in 310 g of deionized water to form PART A. PART B consisted of 40 g (0.132 moles) eicosa-5,7-diynoic acid dissolved in a mixture of 133.6 g of 0.985N sodium hydroxide and 276 g of deionized water at 70° C. PART C was a solution of 9.63 g (0.044 moles) of zinc acetate dihydrate and 6.52 g (0.022 moles) of zinc nitrate hexahydrate dissolved in 84 g of deionized water.

PART A was placed in a jacketed vessel and heated to 50° C. While agitating this gelatin solution, PARTS B and C were added simultaneously at respective rates of about 15 g/min and 3.33 g/min. During the addition period PART B solution was kept at a temperature between about 45° C. and 70° C. The additions of PARTS B and C were each complete in about 30 minutes.

When the additions were complete, a dispersion of sub-micron particles of zinc bis (eicosa-5,7-diynoate) had formed in the gelatin solution. The dispersion was chill set at about 4° C. and refrigerated.

Subsequently, several 20 g portions of the dispersion were taken and melted at 60° C. To these samples were added various small amounts of either a 16.15% solution of zinc acetate or a 8.89% solution of sodium eicosa-5,7-diynoate. The amounts added were sufficient to establish a small stoichiometric excess of one or the other of the materials, relative to the amounts of zinc ion or eicosa-5,7-diynoate ion used in preparing the original dispersion. The dispersion samples with their additional agents were then ripened by slowly agitating the dispersion at 60° C. for 2.5 hours. At intervals during the ripening period small amounts of dispersion were withdrawn and mixed with a small amount of a surfactant serving as a coating aid. These samples were coated with a #46 wire-wound rod on a polyester film base and the coatings were dried. The coatings were then exposed to known mounts of short wavelength UV radiation at about 250 nm to produce sensitometric step tablets. Subsequently, the visual density of the steps on the tablets were measured and the exposure require to produce a visual density of 2.0 du on each sample was calculated. The results are given in the following table.

| Stoichiometric Excess of Additional Agent | Exposure (mJ/cm²) to Produce Density 2.0 | |
|---|---|---|
| | Ripening Time | |
| | 0 hrs | 2.5 hours |
| 7% zinc acetate dihydrate | | 11.5 mj/cm² |
| 5% zinc acetate dihydrate | | 15.0 mj/cm² |
| 2% zinc acetate dihydrate | | 16.0 mj/cm² |
| 0.5% zinc acetate dihydrate | | 16.0 mj/cm² |
| none | 11.0 mj/cm² | 11.0 mj/cm² |
| 0.5% sodium eicosa-5,7-diynoate | | 15.0 mj/cm² |
| 2% sodium eicosa-5,7-diynoate | | 11.0 mj/cm² |
| 5% sodium eicosa-5,7-diynoate | | 6.0 mj/cm² |
| 7% sodium eicosa-5,7-diynoate | | 6.5 mj/cm² |

From the data in the Table, it can be clearly seen that the photosensitivity of the dispersion is very markedly increased by ripening the dispersion with at least about a 5% excess amount of sodium eicosa-5,7-diynoate. No increase, or even a small decrease, in photosensitivity was observed with zinc acetate dihydrate in excess or with smaller excess amounts of sodium eicosa-5,7-diynoate. The increase in sensitivity is particularly dramatic after 2.5 hours. Additional advances in sensitivity can be obtained by extending the ripening to longer times.

A similar ripening effect caused by the addition of a small stoichiometric excess of sodium eicosa-5,7-diynoate was also observed for dispersions similar to that described above, but which were prepared using only zinc acetate dihydrate or only zinc nitrate hexahydrate in the PART C solution.

Additionally, it has been observed that ripening may be effected at temperatures other than 60° C. In general, it has been found that the rate of ripening increases with increasing temperature. Thus at 100° C. an effect on sensitivity similar to that described above is seen after only about 1 hour ripening, while at 40° C., ripening takes more than a day to complete.

EXAMPLE 30

Bilayer Structure Yielding a Neutral, Black Color

A sample of the zinc bis (pentacosa-10,12-diynoate) dispersion described in Example 2 was melted at 40° C. and a small quantity of a coating aid was added. The resulting mixture was coated on a polyester film base using a wire-wound rod. After drying, the coated layer was about 4 μm thick. This coating is of similar composition and similar thermochromic properties to the one described in Example 11, except that it is thinner.

A second 4 μm layer was added to the first layer by over-coating a portion of the washed zinc bis (pentacosa-10,12-diynoate) dispersion and coating as described in Example 12.

When this composite coating was exposed to 254 nm UV radiation, it rapidly developed a deep blue color. Subsequently, when this blue coating was passed around a heated roller at about 110° C. for about 6 seconds and cooled to ambient temperature (20° C.–25° C.), the color had changed from blue to a neutral, black.

This same result was obtained when the positions of the two layers were reversed.

Similar results were also obtained by using the zinc bis (eicosa-5,7-diynoate) dispersion of Example 4 in place of the zinc bis (pentacosa-10,12-diynoate) dispersion used, as described above, to coat the first layer of the composite coating.

EXAMPLE 31

Thermochromism of Ripened Dispersions

A dispersion of zinc bis (eicosa-5,7-diynoate) was prepared by the method in Example 29.

The dispersion was ripened by adding a 2% molar excess of sodium eicosa-5,7-diynoate and heating the mixture at about 50° C. for 24 hours. At various times during the ripening process samples of dispersion were removed and, after addition of a small amount of a surfactant coating aid, the dispersion samples were coated on polyester film base to yield a dry layer of about 8 μm thickness.

A series of 254 nm UV exposures (exposure level E mj/cm$^2$) was made on each coated sample to generate a blue colored sensitometer step tablet. After measuring the visual density (D) of each of the steps, the data was used to plot a sensitometric D-logE curve for each sample. The D-logE curves allow the sensitivity of each sample to be determined by estimating, by interpolation, the exposure required to generate a visual density of 2.0.

From the results shown in the Table, it is evident that the sensitivity increases (i.e. decreased exposure required to produce D=2.0) with increasing ripening time. Furthermore, when the film samples were passed around a hot roller at about 110° C. for 6 seconds, it was observed that the samples exhibited different thermochromic properties. Thus, the samples that had the lowest photosensitivity showed the most dramatic thermochromic color changes from blue to yellow. The more photosensitive samples showed relatively small thermochromic color changes from the original bright blue to a blue-grey color. Viewed together, the samples showed a continuum of thermochromic behavior which was dependent upon the photosensitivity of the dispersion from which the coatings were prepared.

TABLE

| Ripening Time, hrs | Sensitivity, mJ/cm$^2$ | Color After Heat Treatment |
|---|---|---|
| 0 | 34.0 | Yellow |
| 4 | 12.0 | Blue-Green |
| 7.5 | 9.0 | Blue-Green |
| 24 | 4.5 | Blue |

EXAMPLE 32

Neutral, Black Colored Film from a Mixture of Dispersions

A dispersion containing zinc bis (eicosa-5,7-diynoate) was prepared and ripened for about 24 hours with a 2% excess of sodium eicosa-5,7-diynoate as described in Example 29. An 8 μm thick coating of this dispersion had a photosensitivity of about 4 mJ/cm$^2$ (UV exposure at 254 nm required to produce visual density of 2.0.) The initial color of the exposed sample was blue. The sample exhibited negligible thermochromism when passed around a heated roller at about 112° C. for 6 seconds. After the heat treatment, the color was a slightly more neutral grey-blue.

A second dispersion containing zinc bis (pentacosa-10, 12-diynoate) was prepared according to Example 2. The dispersion was not ripened. An 8 μm coating of this dispersion had a photosensitivity of about 10 mJ/cm$^2$ and produced a blue color similar to the zinc bis (eicosa-5,7-diynoate) dispersion described above. However, the exposed coating of the zinc his (pentacosa-10,12-diynoate) dispersion showed a striking thermochromism from blue to yellow when given the same treatment around a 112° C. roller for 6 seconds.

A coating (8 μm dry thickness) was then made from a 1:1 mixture of the dispersions described above. This coating had a photosensitivity of about 6 mJ/cm$^2$ and initially produced a blue image color. However, when this exposed coating was heat treated around the 112° C. roller for 6 seconds, the color changed dramatically from blue to a neutral black.

EXAMPLE 33

Effect of Sodium Carboxylate Salts on Thermochromism

A washed dispersion of zinc bis (eicosa-5,7-diynoate) was prepared using the washing procedure described in Example 12. 10 g portions of this dispersion were taken and small amounts of 1M aqueous solutions of various sodium carboxylates were added. The additions were sufficient to produce about a 1:1 molar ratio of zinc (eicosa-5,7-diynoate) to sodium carboxylate in the sample.

A small amount of FC-129 surfactant coating aid was added to each mixture and coatings were made using a wire-wound rod. When dried, the coatings were about 8 μm thick. The coatings were then exposed to 254 nm UV radiation producing, except in the case of the sample containing sodium hexanoate, the expected blue image color. These exposed samples were then heat treated around a 110° C. roller for about 6 seconds. The thermochromic behavior is noted in Table A.

TABLE A

| Carboxylate | Photosensitivity | Initial Color | Color After Treatment at 100° C. |
|---|---|---|---|
| Control Sample | | | |
| no carboxylate | Control Sample | Blue | Blue |
| Formate | Same as control | Blue | Magenta |
| Propiolate | " | Blue | Red |
| Acetate | " | Blue | Yellow |
| Acrylate | " | Blue | Yellow |
| Propionate | " | Blue | Yellow |
| n-Butyrate | " | Blue | Yellow |
| n-Hexanoate | Much less than control | Purple | Yellow |
| n-Octanoate | Same as control | Blue | Yellow |
| Oxybate | " | Blue | Red |
| Trimethylacetate | " | Blue | Magenta |
| Benzoate | " | Blue | Purple |
| Ethoxyacetate | " | Blue | Yellow |

The effect of the sodium linear carboxylates that conferred blue to yellow thermochromism was further explored. Smaller amounts than the above mentioned 1:1 molar ratio of sodium carboxylate to zinc eicosa-5,7-diynoate were added to dispersion. Coatings were made, dried, exposed to 254 nm UV light and heat treated. The thermochromism was observed. Table B lists the minimum molar ratio of sodium carboxylate:zinc bis (eicosa-5,7-diynoate) that gave blue to yellow thermochromism at 110° C.

TABLE B

| Carboxylate | Minimum Molar Ratio of Carboxylate to Zinc Bis (Eicosa-5,7-Diynoate) Giving Blue to Yellow Thermochromism at 100° C. |
|---|---|
| Sodium Acetate | 1:1 |
| Sodium Acrylate | 1:1 |
| Sodium Propionate | 3:4 |
| Sodium n-Butyrate | 1:2 |
| Sodium n-Hexanoate | 1:4 |
| Sodium n-Octanoate | 1:4 |

From the results in Table B, it is inferred that the activity of linear carboxylates in effecting thermochromism generally increases with increasing alkyl chain lengths, at least up to n-octanoate.

The previously described examples have been provided for purposes of illustration of the present invention only and should not be construed to limit the scope of the invention of the present application as described in the following claims in any way.

What is claimed is:

1. A mixture of radiation imageable polyacetylenic compounds which have similar photosensitivities and which are imageable in complementary colors combinable to form a black or near black image color, said mixture comprising (a) an imageable metal salt of a polyacetylene $C_6$ to $C_{48}$ mono- or dicarboxylic acid which develops a first color and (b) at least one imageable polyacetylene compound capable of developing a second color complementary to said first color.

2. The mixture of claim 1 wherein said imageable metal salt (a) and said imageable polyacetylene compound (b) are included in said mixture at a molar ratio of about 1:2 to about 2:1.

3. The mixture of claim 2 wherein said imageable diacetylene (b) is a $C_6$ to $C_{48}$ mono- or dicarboxylic acid, ester, amide, carbonate, carbamate or cinnamate.

4. The mixture of claim 1 wherein said imageable polyacetylene compound (b) is an imageable metal salt of a diacetylene $C_6$ to $C_{48}$ mono- or dicarboxylic acid.

5. The mixture of claim 1 wherein said imageable polyacetylene compound (b) is an imageable polyacetylene of a $C_6$ to $C_{48}$ mono- or dicarboxylic acid or an ester, amide, carbonate, carbamate or cinnamate derivative thereof.

6. The mixture of claim 1 wherein said imageable polyacetylene (b) is a mixture of at least one imageable metal salt of a polyacetylene $C_6$ to $C_{48}$ monocarboxylic acid and at least one non-metallic diacetylenic compound.

7. The mixture of claim 6 wherein said imageable metal salt (a) is a zinc salt of a diacetylene $C_6$ to $C_{43}$ carboxylic acid.

8. The mixture of claim 6 wherein said imageable metal salt (a) is a zinc salt of a diacetylene $C_{14}$ to $C_{35}$ carboxylic acid.

9. The mixture of claim 6 wherein said imageable metal salt (a) is a metal salt of a polyacetylene $C_6$ to $C_{48}$ mono- or dicarboxylic acid and said imageable polyacetylene compound (b) is a zinc salt of a polyacetylene $C_6$ to $C_{48}$ mono- or dicarboxylic acid, said imageable polyacetylene compound (b) being mixed in combination with an additive selected from the group consisting of a $C_2$ to $C_8$ linear alkyl carboxylate, a nitrate anion and mixtures, thereof, at a weight ratio of about 4:1 to about 1:20 by weight of said imageable polyacetylene compound (b).

10. The mixture of claim 9 wherein said imageable metal salt (a) is a zinc salt of a polyacetylene $C_{14}$ to $C_{43}$ monocarboxylic acid imageable to a blue color and said imageable polyacetylene (b) is a zinc salt of a polyacetylene $C_{14}$ to $C_{43}$ monocarboxylic acid imageable to a yellow color.

11. The mixture of claim 1 wherein said metal salt (a) contains a metal cation having an atomic weight ranging from about 7 to about 180.

12. The mixture of claim 1 wherein said imageable metal salt (a) contains a metal cation selected from the group consisting of Li, Zn, Rb, Ba, Mn, Zr, Mg, Ca, Tl, Te and Tm.

13. The mixture of claim 1 wherein said imageable metal salt (a) is an unbranched compound.

14. A mixture of radiation imageable polyacetylenic compounds which have similar photosensitivities and which are imageable in complementary colors combinable to form a permanent black or near black image color, said mixture comprising (a) an imageable metal salt of a polyacetylene $C_6$ to $C_{48}$ mono or dicarboxylic acid which develops a first color and (b) at least one imageable polyacetylene compound capable of developing a second color complementary to said first color, said imageable metal salt and said imageable polyacetylene compound being combined as crystals in a molar ratio of about 10:1 to about 1:10 with an amount of a binder effective to substantially eliminate agglomeration of said crystals.

15. The mixture according to claim 14 wherein said binder is included in a weight ratio ranging from about 1:10 to about 10:1 by weight of said imageable metal salt (a) and said imageable polyacetylene compound (b).

16. The mixture of claim 14 wherein said imageable polyacetylene compound (b) is an imageable metal salt of a diacetylene $C_6$ to $C_{48}$ mono- or dicarboxylic acid.

17. The mixture of claim 14 wherein said imageable polyacetylene compound (b) is an imageable polyacetylene of a $C_6$ to $C_{48}$ mono- or dicarboxylic acid or an ester, amide, carbonate, carbamate or cinnamate derivative of said mono- or dicarboxylic acid.

18. The mixture of claim 14 wherein wherein said imageable polyacetylene (b) is a mixture of at least one imageable metal salt of a polyacetylene $C_6$ to $C_{48}$ monocarboxylic acid and at least one non-metallic polyacetylenic compound.

19. The mixture of claim 14 wherein said metal salt (a) contains a metal cation having an atomic weight ranging from about 7 to about 180.

20. The mixture of claim 14 wherein said imageable metal salt (a) contains a metal cation selected from the group consisting of Li, Zn, Rb, Ba, Mn, Zr, Mg, Ca, Tl, Te and Tm.

21. The mixture of claim 20 wherein said imageable metal salt (a) is a zinc salt.

22. The mixture of claim 20 wherein said imageable metal salt (a) is a zinc salt of a diacetylene $C_{15}$ to $C_{35}$ mono- or dicarboxylic acid.

23. The mixture of claim 14 wherein said imageable metal salt (a) is an unbranched compound.

24. The mixture of claim 14 wherein said imageable metal salt (a) is a metal salt of a $C_6$ to $C_{48}$ monocarboxylic acid and said imageable polyacetylene compound (b) is a zinc salt of a diacetylene $C_6$ to $C_{48}$ monocarboxylic acid, said imageable polyacetylene compound (b) being mixed in combination with an additive selected from the group consisting of a $C_2$ to $C_8$ linear alkyl carboxylate, a nitrate anion, or mixtures, thereof at a weight ratio of about 4:1 to about 1:20 by weight of said imageable polyacetylene compound.

25. The mixture according to claim 24 wherein said first color is blue and said second color is yellow.

26. The mixture according to claim 14 further including an amount of a polyethyleneoxide or polypropyleneoxide containing compound ranging from about 0.01% to about 1% by weight of said mixture.

27. The mixture according to claim 14 further including a film-forming polymer.

28. An imageable laminate comprising a first layer of a support and a second layer comprising the composition of claim 14.

29. A method for imaging the laminate of claim 28 comprising subjecting the laminate to irradiation to which the composition is sensitive and then heating the exposed laminate at a temperature and for a time period sufficient to produce a permanent black image color.

30. The method according to claim 29 wherein said temperature is at least about 100C.° and said time period is at least about 1 microsecond.

31. An imaged laminate obtained by the method of claim 29.

32. A method of producing a permanent black or near black image color in combination with a colorless image from the mixture of claim 14, said method comprising exposing a first portion of said mixture to heat energy, then exposing at least a second portion of said entire mixture to ionizing radiation and then to heat.

33. The method according to claim 32 wherein said ionizing radiation is generated from an electron beam, mercury xenon arc lamp, mercury arc lamp, xenon flash lamp, actinic light, neutrons, x-rays, gamma rays, beta rays, alpha particles, electron corona discharge, or UV laser source.

34. A composition comprising at least two distinct layers, at least one first layer comprising crystals of at least one imageable metal salt of a polyacetylene $C_6$ to $C_{48}$ mono- or dicarboxylic acid capable of developing a first color, in combination with at least one binder in an amount effective to substantially eliminate agglomeration of said crystals; and
at least one additional layer comprising crystals of at least one imageable polyacetylene compound capable of developing a second color complementary to said first color in said first layer, in combination with at least one binder in an amount effective to substantially eliminate agglomeration of said crystals.

35. The composition according to claim 34 wherein said binder is included in said first layer in a weight ratio ranging from about 1:10 to about 10:1 by weight of said imageable metal salt.

36. The composition of claim 34 wherein said imageable polyacetylene compound (b) is an imageable polyacetylene of a $C_6$ to $C_{48}$ mono- or dicarboxylic acid or an ester, amide, carbonate, carbamate or cinnamate derivative thereof.

37. The composition of claim 34 wherein said imageable polyacetylene compound included in said second layer is also an imageable metal salt of a polyacetylene $C_6$ to $C_{48}$ monocarboxylic acid.

38. The composition of claim 34 wherein said imageable polyacetylene included in said second layer is a composition comprising at least one imageable metal salt of a polyacetylene $C_6$ to $C_{48}$ monocarboxylic acid and at least one nonmetallic polyacetylenic compound.

39. The mixture of claim 34 wherein said metal salt (a) contains a metal cation having an atomic weight ranging from about 7 to about 180.

40. The composition of claim 34 wherein said imageable metal salt contains a metal cation selected from the group consisting of Li, Zn, Rb, Ba, Mn, Zr, Mg, Ca, Tl, Te and Tm.

41. The composition of claim 40 wherein said imageable metal salt is a zinc salt.

42. The composition of claim 40 wherein said imageable metal salt is a zinc salt of a diacetylene $C_{14}$ to $C_{43}$ monocarboxylic acid.

43. The composition of claim 34 wherein said imageable metal salt is an unbranched compound.

44. The composition of claim 34 wherein said imageable metal salt in said first layer is a metal salt of a $C_6$ to $C_{48}$ mono- or dicarboxylic acid and said imageable polyacetylene compound in said second layer is a zinc salt of a polyacetylene $C_6$ to $C_{48}$ mono- or dicarboxylic acid, said imageable polyacetylene compound being mixed in combination with a concentration of a carboxylate or nitrate anion at a weight ratio of about 4:1 to about 1:20 by weight of said imageable diacetylene compound.

45. The composition of claim 34 further including an amount of a nonionic polyethyleneoxide or polypropyleneoxide containing compound ranging from about 0.01% to about 1% by weight of said composition in at least one of said layers.

46. The composition according to claim 34 further including a film-forming polymer in either of said layers.

47. The composition of claim 34 wherein said imageable metal salt (a) is a zinc salt imageable to a blue color and said imageable polyacetylene (b) is a zinc salt of a polyacetylene $C_{15}$ to $C_{43}$ monocarboxylic acid imageable to a yellow color.

48. An imageable laminate comprising a first layer of support and the composition of claim 29.

49. A method for imaging the laminate of claim 48 comprising subjecting the laminate to irradiation to which the composition is sensitive and then heating the exposed laminate at a temperature and for a time period sufficient to produce a permanent black image color.

50. The method according to claim 49 wherein said temperature is at least about 100 C°.

51. The method according to claim 50 wherein said time period is at least about one microsecond.

52. An imaged laminate obtained by the method of claim 49.

53. An imageable laminate comprising a first layer of a support, a second layer of an imageable metal salt of a diacetylene $C_6$ to $C_{45}$ monocarboxylic acid imageable to a first color, and a third layer comprising at least one polyacetylene compound imageable to a second color, said imageable metal salt of said second layer and said imageable polyacetylene compound of said third layer having similar photosensitivities, said first color and said second color being complementary and combinable to form a black or near black image color when viewed in the laminate.

54. A method for imaging the laminate of claim 53 comprising subjecting the laminate to irradiation to which the composition is sensitive and then heating the exposed laminate at a temperature and for a time period sufficient to produce a permanent black image color.

55. An imaged laminate obtained by the method of claim 54.

56. A method of producing a permanent black or near black image color comprising exposing a mixture of radiation imageable polyacetylenic compounds which have similar photosensitivities and which are imageable in complementary colors combinable to form a black or near black image color, said mixture comprising (a) a imageable metal salt of a polyacetylene $C_6$ to $C_{48}$ monocarboxylic acid which develops a first color and (b) at least one imageable polyacetylene compound capable of developing a second color complementary to said first color,
said method comprising exposing said mixture first to ionizing radiation and then to heat energy.

57. The method according to claim 56 wherein said ionizing radiation is generated from an electron beam, mercury xenon arc lamp, mercury arc lamp, xenon flash lamp, actinic light, neutrons, x-rays, gamma rays, beta rays, alpha particles, electron corona discharge, or UV laser source.

58. The method according to claim 56 wherein said imageable metal salt (a) and said imageable polyacetylene compound (b) are included in said method at a molar ratio of about 1:10 to about 10:1.

59. The method according to claim 56 wherein said imageable metal salt (a) and said imageable polyacetylene compound (b) are included in said method at a molar ratio of about 1:2 to about 2:1.

60. The method according to claim 56 wherein said imageable metal salt (a) is a metal salt of a $C_6$ to $C_{48}$ monocarboxylic acid and said imageable polyacetylene compound (b) is a zinc salt of diacetylene $C_6$ to $C_{40}$ monocarboxylic acid, said imageable polyacetylene compound (b) being mixed in combination with a concentration of a carboxylate or nitrate anion at a weight ratio of about 4:1 to about 1:20 by weight of said imageable polyacetylene compound (b).

61. The method according to claim 56 comprising exposing a portion of said mixture to a heat step before exposing said mixture to ionizing radiation followed by heat.

62. The method according to claim 56 wherein said heat step is conducted at a temperature of at least about 100° C. and for a time period of at least about 1 microsecond.

63. An imageable laminate comprising:
1. a first layer of a support;
2. a second layer of an imageable metal salt of a polyacetylene $C_6$ to $C_{48}$ mono- or dicarboxylic acid which develops a first color; and
3. at least one additional layer comprising at least one imageable polyacetylene compound capable of developing one or more colors which, in combination, are complementary to said first color in said second layer, said imageable metal salt of said second layer and said imageable polyacetylene compound of said additional layer having similar photosensitivities, said first color and said one or more colors being combinable to form a black or near black image color when viewed in the laminate.

64. A laminate comprising
1. a first layer of a support;
2. a second layer comprising an imageable metal salt of a polyacetylene $C_6$ to $C_{48}$ mono- or dicarboxylic acid in combination with a first polyacetylenic polymer providing a first color; and
3. at least one additional layer comprising at least one imageable polyacetylene compound in combination with at least one additional polyacetylenic polymer providing a color or colors which are complementary to said first color in said second layer, said first polyacetylenic polymer and said additionals polyacetylenic polymer in combination producing a permanent black or near-black image color in the form of a design.

65. A mixture of an imageable zinc metal salt of a polyacetylene $C_6$ to $C_{48}$ mono- or di-carboxylic acid in combination with an additive selected from the group consisting of a $C_2$ to $C_8$ sodium carboxylate, a sodium nitrate anion and mixtures, thereof, at a weight ratio of about 4:1 to about 1:20 by weight of said imageable metal salt.

66. The mixture according to claim 65 wherein said carboxylic acid is a $C_{14}$ to $C_{43}$ diacetylenic mono- or dicarboxylic acid.

67. The mixture according to claim 65 wherein said additive is a mixture of a $C_2$ to $C_8$ sodium linear alkyl carboxylate and sodium nitrate.

68. The mixture according to claim 67 wherein said carboxylic acid is a $C_{15}$ to $C_{35}$ diacetylenic monocarboxylic acid.

69. The mixture according to claim 68 further in combination with a binder.

70. The mixture according to claim 69 in combination with a polyethyleneoxide or polypropylene oxide containing compound ranging from about 0.01% to about 1% by weight of said mixture.

71. The mixture according to claim 70 wherein said zinc salt is zinc bis(eicosa-5,7-diyonate).

72. A laminate comprising a first layer of support and at least one additional layer comprising the mixture of claim 70.

73. A laminate comprising a first layer of support and at least one additional layer comprising the mixture of claim 69.

74. The mixture according to claim 65 further in combination with a binder.

75. The mixture according to claim 74 in combination with a polyethyleneoxide or polypropylene oxide containing compound ranging from about 0.01% to about 1% by weight of said mixture.

76. A laminate comprising a first layer of support and at least one additional layer comprising the mixture of claim 75.

77. A laminate comprising a first layer of support and at least one additional layer comprising the mixture of claim 65.

78. A method of producing a permanent black or near black image color in combination with a colorless image from the mixture of claim 65, said method comprising exposing a first portion of said mixture to heat energy, then exposing at least a second portion of said mixture to ionizing radiation and then to heat energy.

79. The method according to claim 78 wherein said ionizing radiation is generated from an electron beam, mercury xenon arc lamp, mercury arc lamp, xenon flash lamp, actinic light, neutrons, x-rays, gamma rays, beta rays, alpha particles, electron corona discharge, or UV laser source.

80. A method of producing a permanent black or near black image color from the mixture of claim 65, said method comprising exposing said mixture to ionizing radiation and then to heat.

81. The method according to claim 80 wherein said ionizing radiation is generated from an electron beam, mercury xenon arc lamp, mercury arc lamp, xenon flash lamp, actinic light, neutrons, x-rays, gamma rays, beta rays, alpha particles, electron corona discharge, or UV laser source.

82. The method according to claim 81 wherein said heat is applied at a temperature of at least about 100° C.

83. The method according to claim 80 wherein said heat is applied at a temperature of at least about 50° C.

84. A laminate comprising
1. a first layer of a support; and
2. a second layer comprising a mixture of an imageable zinc salt of a polyacetylene $C_6$ to $C_{48}$ mono- or di-carboxylic acid in combination with an additive selected from the group consisting of a $C_2$ to $C_8$ sodium linear alkyl carboxylate, sodium nitrate and mixtures, thereof, at a weight ratio of about 4:1 to about 1:20 by weight of said imageable metal salt, in combination with at least one polyacetylenic polymer providing a permanent black or near-black image color in the form of a design.

85. The laminate according to claim 84 wherein said carboxylic acid is a $C_{15}$ to $C_{35}$ diacetylenic mono- or dicarboxylic acid.

86. The laminate according to claim 84 wherein said additive is a mixture of a $C_2$ to $C_8$ sodium carboxylate anion and a sodium nitrate anion.

87. The laminate according to claim 86 wherein said carboxylic acid is a $C_{15}$ to $C_{35}$ diacetylenic monocarboxylic acid.

88. The laminate according to claim 87 wherein said mixture is further combined with a binder.

89. The laminate according to claim 88 in wherein said mixture contains a polyethyleneoxide or polypropylene oxide containing compound ranging from about 0.01% to about 1% by weight.

90. The laminate according to claim 89 wherein said zinc salt is zinc bis(eicosa-5,7-diyonate).

91. The laminate according to claim 84 wherein said mixture is further combined with a binder.

92. The laminate according to claim 84 wherein said mixture contains a polyethyleneoxide or polypropylene oxide containing compound ranging from about 0.01% to about 1% by weight.

* * * * *